(12) United States Patent
Chu et al.

(10) Patent No.: US 10,533,008 B2
(45) Date of Patent: Jan. 14, 2020

(54) SYNTHESIS OF 2'-FLUORO-6'-METHYLENE-CARBOCYCLIC ADENOSINE (FMCA) AND 2'-FLUORO-6'-METHYLENE-CARBOCYCLIC GUANOSINE (FMCG)

(71) Applicant: UNIVERSITY OF GEORGIA RESEARCH FOUNDATION, IONC., Athens, GA (US)

(72) Inventors: Chung K. Chu, Stratham, GA (US); Varughese Alexander Mulamoottil, Athens, GA (US); Ram C. Mishra, Conyers, GA (US); Uma Sharan Singh, Athens, GA (US)

(73) Assignee: UNIVERSITY OF GEORGIA RESEARCH FOUNDATION, INC., Atlanta, GA (US)

( * ) Notice: Subject to any disclaimer, the term of this patent is extended or adjusted under 35 U.S.C. 154(b) by 0 days.

(21) Appl. No.: 16/083,128

(22) PCT Filed: Mar. 1, 2017

(86) PCT No.: PCT/US2017/020165
§ 371 (c)(1),
(2) Date: Sep. 7, 2018

(87) PCT Pub. No.: WO2017/176392
PCT Pub. Date: Oct. 12, 2017

(65) Prior Publication Data
US 2019/0100523 A1    Apr. 4, 2019

Related U.S. Application Data

(60) Provisional application No. 62/319,694, filed on Apr. 7, 2016.

(51) Int. Cl.
| | |
|---|---|
| *C07D 473/34* | (2006.01) |
| *C07D 317/44* | (2006.01) |
| *C07C 41/26* | (2006.01) |
| *C07C 41/30* | (2006.01) |
| *C07D 473/18* | (2006.01) |
| *C07D 473/26* | (2006.01) |
| *C07D 473/40* | (2006.01) |
| *C07F 9/6561* | (2006.01) |
| *C07C 41/28* | (2006.01) |
| *A61P 31/20* | (2006.01) |
| *C07C 43/196* | (2006.01) |

(52) U.S. Cl.
CPC ............ *C07D 473/34* (2013.01); *C07C 41/26* (2013.01); *C07C 41/28* (2013.01); *C07C 41/30* (2013.01); *C07D 317/44* (2013.01); *C07D 473/18* (2013.01); *C07D 473/26* (2013.01); *C07D 473/40* (2013.01); *C07F 9/65616* (2013.01); *A61P 31/20* (2018.01); *C07C 43/196* (2013.01); *C07C 2601/08* (2017.05)

(58) Field of Classification Search
CPC .................................................... C07D 473/34
USPC .......................................................... 544/277
See application file for complete search history.

(56) References Cited

FOREIGN PATENT DOCUMENTS

| WO | 2011060408 A2 | 5/2011 |
|---|---|---|
| WO | 2012158552 A2 | 11/2012 |

OTHER PUBLICATIONS

Bhattacharya, D.; Thio, C. L. Clinical Infectious Diseases 2010, 51, 1201.
Kim, K. H.; Kim, N. D.; Seong, B. L. Molecules 2010, 15, 5878.
Mukaide, M.; Tanaka, Y.; Shin-I, T.; Yuen, M. F.; Kurbanov, F.; Yokosuka, O.; Sata, M.; Karino, Y.; Yamada, G.; Sakaguchi, K.; Orito, E.; Inoue, M.; Baqai, S.; Lai, C. L.; Mizokami, M. Antimicrob. Agents Ch 2010, 54, 882.
Bartholomeusz, A.; Locarnini, S. Journal of Medical Virology 2006, 78, S52.
Wang, J. N.; Singh, U. S.; Rawal, R. K.; Sugiyama, M.; Yoo, J.; Jha, A. K.; Scroggin, M.; Huang, Z. H.; Murray, M. G.; Govindarajan, R.; Tanaka, Y.; Korba, B.; Chu, C. K. Bioorg. Med. Chem. Lett. 2011, 21, 6328.
Rawal, R. K.; Singh, U. S.; Chavre, S. N.; Wang, J. N.; Sugiyama, M.; Hung, W.; Govindarajan, R.; Korba, B.; Tanaka, Y.; Chu, C. K. Bioorg. Med. Chem. Lett. 2013, 23, 503.
Walsh, A. W.; Langley, D. R.; Colonno, R. J.; Tenney, D. J. PLoS. One 2010, 5.
Jin, Y. H.; Liu, P.; Wang, J. N.; Baker, R.; Huggins, J.; Chu, C. K. J. Org. Chem. 2003, 68, 9012.
Jin, Y. H.; Chu, C. K. Nucleos. Nucleot. Nucl. 2003, 22, 771.
Gadthula, S.; Rawal, R. K.; Sharon, A.; Wu, D.; Korba, B.; Chu, C. K. Bioorg. Med. Chem. Lett. 2011, 21, 3982.
Fung, J.; Lai, C. L.; Seto, W. K.; Yuen, M. F. J Antimicrob Chemoth 2011, 66, 2715.

(Continued)

*Primary Examiner* — Jeffrey H Murray
(74) *Attorney, Agent, or Firm* — Henry D. Coleman; R. Neil Sudol

(57) ABSTRACT

The invention provides a new convergent approach for the synthesis of 2'-fluoro-6'-methylene-carbocyclic adenosine (FMCA) and 2'-fluoro-6'-methylene-carbocyclic guanosine (FMCG) from a readily available starting material in eight steps. An efficient and practical methodology for stereospecific preparation of a versatile carbocyclic key intermediate, (1S,3R,4R)-3-tert-butoxy-4-(tert-butoxymethyl)-2-fluoro-5-methylenecyclopentanol (compound 8 of scheme 1A or a) in only six (6) steps is also provided. Prodrugs of these compounds are also prepared.

11 Claims, 4 Drawing Sheets

(56) References Cited

OTHER PUBLICATIONS

Tenney, D. J.; Rose, R. E.; Baldick, C. J.; Levine, S. M.; Pokornowski, K. A.; Walsh, A. W.; Fang, J.; Yu, C. F.; Zhang, S.; Mazzucco, C. E.; Eggers, B.; Hsu, M.; Plym, M. J.; Poundstone, P.; Yang, J.; Colonno, R. J. Antimicrob Agents Ch 2007, 51, 902.

Terrault, N. A.; Bzowej, N. H.; Chang, K. M.; Hwang, J. P.; Jonas, M. M.; Murad, M. H. Hepatology 2016, 63, 261.

Bin Lee, Y.; Lee, J. H.; Lee, D. H.; Cho, H.; Ahn, H.; Choi, W. M.; Cho, Y. Y.; Lee, M.; Yoo, J. J.; Cho, Y.; Cho, E. J.; Yu, S. J.; Kim, Y. J.; Yoon, J. H.; Kim, C. Y.; Lee, H. S. Hepatology 2014, 60, 1115a.

Lazarevic, I. World J Gastroentero 2014, 20, 7653.

McGuigan, C.; Gilles, A.; Madela, K.; Aljarah, M.; Holl, S.; Jones, S.; Vernachio, J.; Hutchins, J.; Ames, B.; Bryant, K. D.; Gorovits, E.; Ganguly, B.; Hunley, D.; Hall, A.; Kolykhalov, A.; Liu, Y. L.; Muhammad, J.; Raja, N.; Walters, R.; Wang, J.; Chamberlain, S.; Henson, G. J Med Chem 2010, 53, 4949.

Chang, W.; Bao, D. H.; Chun, B. K.; Naduthambi, D.; Nagarathnam, D.; Rachakonda, S.; Reddy, P. G.; Ross, B. S.; Zhang, H. R.; Bansal, S.; Espiritu, C. L.; Keilman, M.; Lam, A. M.; Niu, C.; Steuer, H. M.; Furman, P. A.; Otto, M. J.; Sofia, M. J. Acs Med Chem Lett 2011, 2, 130.

Singh, U. S.; Mishra, R. C.; Shankar, R.; Chu, C. K. J Org Chem 2014, 79, 3917.

Velasco, J.; Ariza, X.; Badia, L.; Bartra, M.; Berenguer, R.; Farras, J.; Gallardo, J .; Garcia, J.; Gasanz, Y. J Org Chem 2013, 78, 5482.

Zhou, B.; Li, Y. C. Tetrahedron Lett 2012, 53, 502.

Bugarin, A.; Jones, K. D.; Connell, B. T. Chem Commun 2010, 46, 1715.

Gemal, A. L.; Luche, J. L. J Am Chem Soc 1981, 103, 5454.

Takano, S.; Ohkawa, T.; Ogasawara, K. Tetrahedron Lett 1988, 29, 1823.

Gadthula, Srinivas et al.; Synthesis and antiviral activity of cyclopropyl-spiro-carbocyclic adenosine, (4R,5S,6R,7R)-4-(6-amino-9H-purin-9-yul)-7-(hydroxymetahyl)spiro[2.4]heptane-5,6-diol against hepatitis C virus. Bioorganic & Medicinal Chemistry Letters, 2011, vol. 21, No. 13, pp. 3982-3985.

Rawal, Ravindra K. et al.; 2'-Fluoro-6'-methylene-carbocyclic adenosine phosphoramidate (FMCAP) prodrug: In vitro anti-HBV activity against the lamivudine-entecavir resistant triple mutant and its mechanism of action. Bioorganic & Medicinal Chemistry Letters, 2013, vol. 23, No. 2, pp. 503-506.

Singh, Uma S. et al.; Stereoselective Synthesis of 2'-Fluoro-6'-methylene Carbocyclic Adenosine via Vince Lactam. Journal of Organic Chemistry, 2014, vol. 79, No. 9, pp. 3917-3923.

SCHEME 1A

SCHEME 1

SCHEME 2
Synthesis of FMCA and FMCAP from common intermediate (8)

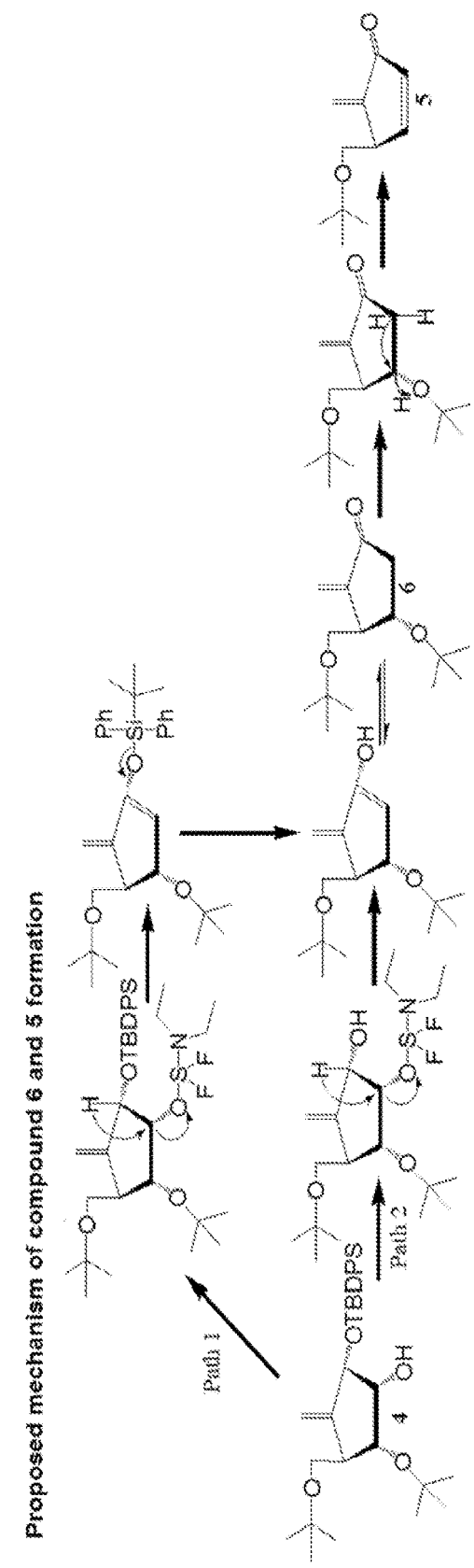

SYNTHESIS OF 2'-FLUORO-6'-METHYLENE-CARBOCYCLIC ADENOSINE (FMCA) AND 2'-FLUORO-6'-METHYLENE-CARBOCYCLIC GUANOSINE (FMCG)

RELATED APPLICATIONS

This application is a United States national phase patent application based on international patent application number PCT/US2017/020165 filed on Mar. 1, 2017, which claims the benefit of priority of U.S. provisional application No. US62/319,694, of identical title, filed Apr. 7, 2016, the entire contents of which said two applications is incorporated by reference herein.

FIELD OF THE INVENTION

The invention provides a new approach for the synthesis of 2'-fluoro-6'-methylene-carbocyclic adenosine (FMC) and 2'-fluoro-6'-methylene-carbocyclic guanosine (FMCG) from a readily available starting material in only eight (8) steps for each compound. An efficient and practical methodology for stereospecific preparation of a versatile carbocyclic key intermediate, (1S,3R,4R)-3-tert-butoxy-4-(tert-butoxymethyl)-2-fluoro-5-methylenecyclopentanol (compound 8 of schemes 1A and 1) in only six (6) steps is also provided. Compound 7 may be readily converted to FMCA or FMCG in only two additional steps in each case.

BACKGROUND OF THE INVENTION

Hepatitis B virus (HBV) is one of the leading causes of morbidity and mortality of human population in all over the world. According to WHO, 2 billion people have been infected with HBV, out of them approximately 3.5 million people are suffering from the chronic HBV infection.[1] Due to severe infection of this virus, worldwide annually 0.5-1.2 million deaths are reported. The untreated HBV infection can develop in liver failure, cirrhosis and eventually hepatocellular carcinoma that result in an urgent need for liver transplantation. However, various drugs and vaccines have introduced for the treatment of the HBV infection, but none of them became a successful candidate for complete eradication of this virus.[2] A particular class of nucleos(t)ides are accessible for the treatment of HBV infection.[3] Theses nucleos(t)ides inhibit viral reverse transcriptase (RT)/DNA polymerase which is an essential enzyme for DNA synthesis in the virus. Based on similar mechanism Lamivudine was first introduced for HBV treatment. After a period of therapy lamivudine-resistant HBV (LVDr) was observed in a significant number of patients.[4] Now a day's Entecavir and Tenofovir are most prescribed drugs for HBV treatment.[5] A long-term therapy of these drugs promotes double and triples mutation in virus and becomes drug-resistant HBV.[6] Recently, reported a triple mutation in the virus (L180M+M204V+S202G) limits the use of entecavir/lamivudine.[7] These double and triple mutations in virus have become a major challenge for the treatment of HBV.[8] There are no any drugs that can suppress the resistance of virus, and these hurdles restrain treatment of resistant HBV. So it is in high demand for researchers to discover a new molecule that can fight against these mutations and provide a success full treatment for HBV.

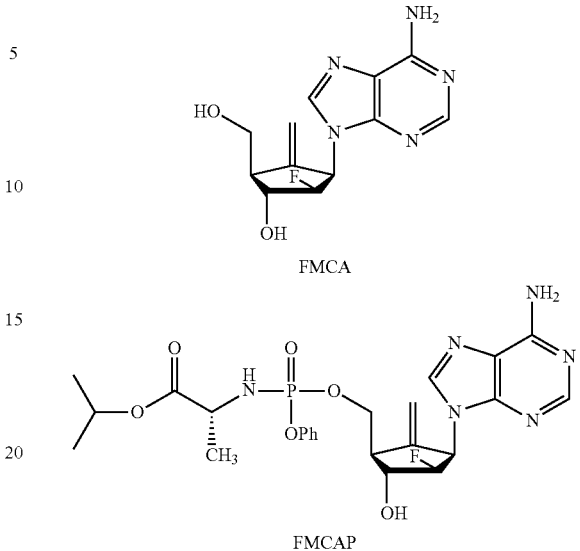

Structures of FMCA and it's phosphoramidate prodrug FMCAP.

FMCA

FMCAP

Since past two decades in search of new moieties for antiviral agents, our group has involved in the discovery of fluoro-containing nucleoside. To overcome the drug resistant problem of HBV, we invented 2'-fluoro-6'-methylene-carbocyclic adenosine (FMCA) and its monophosphate pro-drug (FMCAP, above figure). FMCA has demonstrated a significant activity against wild-type as well as lamivudine, adefovir, and double lamivudine/entecavir-resistant mutants.[9] Furthermore, it has tested against lamivudine/entecavir-resistant clone (L180M+M204V+S202G) that has become a core challenge for presently use drugs for the treatment of HBV. Fortunately, FMCA demonstrated potential antiviral activity against wild-type as well as lamivudine/entecavir-resistant. In many cases, it has well observed and reported in the literature that mono-phosphorylation is the rate limiting step for the activity of parental nucleoside.[10,11] So the monophosphate prodrug of FMCA was synthesized and surprisingly pro-drug (FMCAP) has demonstrated a 12-fold increase in anti-HBV activity against triple mutant core (L180M+M204V+S202G) of entecavir/lamivudine-resistant.[12] The investigations of mitochondrial and cellular toxicity studies of FMCA have also done, and there is no significant toxicity has observed up to 100 µM. By the finding of the above results, it has become a great interest to examine expanded in-vivo activities of FMCA against drug-resistant HBV. Therefore, for further biological screening large quantities of FMCA was required. Consequently, development of a most possible, realistic and cost effect synthesis of FMCA was in urgent need.

However, in our previous communication, we have reported the synthesis of FMCA via Vince lactam in 14 steps.[13] But due to the low yield of certain steps limits this process for the large scale synthesis. Furthermore, the lack of commercial availability of carbocyclic sugar 1 was also a prime challenge for the synthesis of these kinds of carbocyclic based nucleos(t)ide. Our group focused on the synthesis of carbocyclic nucleoside from D-ribose and a convenient method has been reposed.[14] Many commercial vendors adopted this synthesis and now the supply of carbocyclic ketone 1 is readily available on demand. Therefore, herein we report a highly practical synthesis of FMCA in 7 steps by using carbocyclic sugar 1. The straightforward handling of reactions, enclosing with fewer steps approach and use of cheap reagents makes this synthesis more convenient for scalable synthesis of FMCA. This synthesis may easily be used for the large-scale synthesis of FMCA and its pro-drug FMCAP. During the standardization of this synthesis, an interesting 2'-deoxy-carbocylic sugar 5, and 6 were obtained. It is noteworthy that synthesis of 2-deoxy carbocyclic sugars is very critical. The preparation of 2-deoxy carbocyclic sugars requires robust, expensive synthesis for the construction of this kind of sugar. This process may be used for the synthesis of 2-deoxy sugars. In addition compound 6 is attractive carbocyclic sugar intermediate that can be utilized in the scalable synthesis of entecavir[15,16], as well as in the synthesis of other 2'-deoxy-carbocylic nucleos(t)ides. Compound 5 may also serve as the core carbocyclic sugar for the construction of various diversified nucleos(t)ides, those can be tested against a variety of harmful viruses, which are the major threat to humans life.

SUMMARY OF THE INVENTION

The invention provides a new convergent approach for the synthesis of FMCA and FMCG from a common readily available starting material in only eight steps in high yield. The new convergent approach for efficient and scalable synthesis of FMCA in eight steps constitutes a highly efficient and practical method for making the key anti-HBV agent FMCA and the related FMCG, which also exhibits antiviral activity. In an additional embodiment, the first step of the synthesis (to from compound 2) has been modified to provide an increase in the efficiency of the synthetic method and to make the synthesis of compound 2 from compound 1 rather facile and far less problematic and in high yield (70% or greater from compound 1).

In one embodiment, the invention provides a process for synthesizing a compound of formula 7:

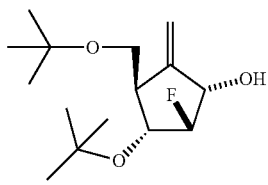

7

From substituted pentanone derivative 1:

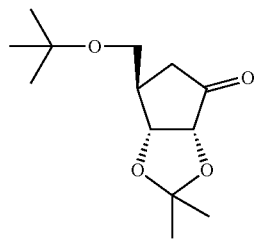

1

Comprising introducing a methylene group in a position α to the keto group of compound 1 by reacting compound 1 with a strong base in solvent at low temperature (e.g., −78° C.) followed by the addition of Eschenmoser Salt and thereafter, iodomethane to provide compound 2A below, which may be isolated, but is preferably reduced in situ using sodium borohydride to provide compound 2;

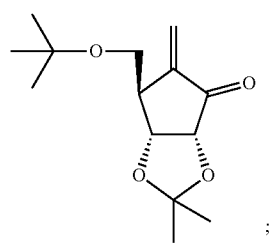

2

Or alternatively and preferably, compound 1

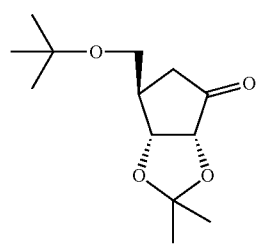

1 is treated with paraformaldehyde $(HCHO)_4$ in the presence of diisopropyl ammonium trifluoracetate salt and diisopropylamine in solvent (e.g. THF) at elevated temperature (preferably, reflux) to introduce a double bond (an olefin group) at position 5 of the cyclopentane ring in compound 1 to provide compound 2A

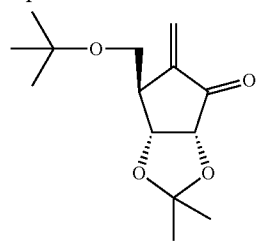

2A in high yield (at least 60% from compound 1, more often at least 70% from compound 1), which is optionally purified by chromatography (e.g. silica gel column 5% EtOAc/hexane) but preferably is reduced in situ without further purification using a reducing agent (e.g. sodium borohydride) and a Lewis acid (e.g., $CeCl_3.7H_2O$) in solvent (e.g. methanol) preferably the keto group of compound 2A is stereoselectively reduced using sodium borohydride in the presence of $CeCl_3$ in solvent (e.g., DCA) at reduced temperature to produce compound 2

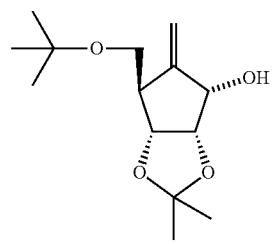

2 which is optionally and preferably isolated (e.g. silica gel column chromatography) in high yield in a single pot over two steps (at least about 50%, preferably 52% or more);

Compound 2 is then reacted with trialkyl aluminum (preferably, AlMe₃) in solvent (e.g. THF, DCM/hexane) at room temperature (initially at low temperature to add the trialkyl aluminum to compound 2 and the reaction mixture was allowed to warm) over a period of 24 hours to several days/72 hours to produce compound 3, which is optionally isolated in greater than 70% yield (to free the 2-hydroxyl group which had been protected and methylating the ether formed by the hydrolysis of the isopropylidene group, thus forming a t-butyl ether group as indicated in compound 3, below),

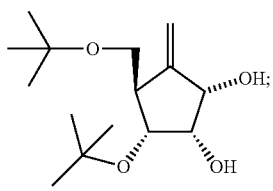

3

Compound 3 is reacted with a sterically hindred silyl protecting group precursor (preferably, tert-butyldiphenyl-silyl chloride) in solvent (e.g. DCM) to produce compound 4, which is optionally purified and isolated (in greater than 70% yield)

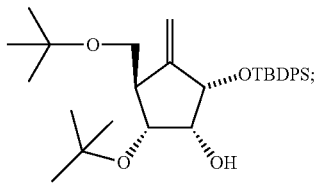

4

Compound 4 is reacted with a fluorinating agent (e.g. diethylaminosulfur trifluoride DAST) in anhydrous solvent (e.g. methylene chloride) to stereoselectively fluorinate the 2' position to produce compound 7, below (the reaction to produce compound 7 also produces compound 6 and compound 5 as side products, see FIG. 1, Scheme 1A and FIG. 2, Scheme 1)

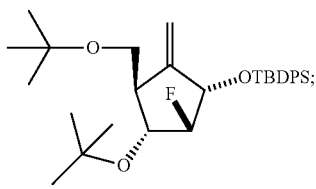

7 which is then reacted to remove the silyl protecting group using tetrabutylammonium fluoride (TBAF) in solvent (e.g., THF) to provide compound 8 below:

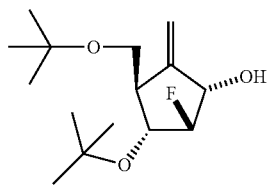

7 wherein one or more steps of the synthesis or the whole synthesis may be conducted in a single pot or in steps, with separation and/or purification of each compound to produce any one or more of compounds 2A, 2, 3, 4, 7 and 8 (compounds 5 and 6, side products, may also be separated/purified). Note that alternative protecting groups other than t-butyl ether protecting groups may be used to produce the sugar synthon (compound 8).

In additional embodiments, compound 8 may be converted to FMCA (compound 10) or FMCG (compound 11), each in as few as two synthetic steps from compound 8. See FIG. 1, Scheme 1A or FIG. 3, Scheme 2.

FMCA (compound 10) is prepared from compound 8 as indicated in FIG. 1, Scheme 1A or FIG. 3, Scheme 2, by condensing an amine protected adenine compound (preferably, the amine protecting group is a BOC group, but may be other amine protecting groups as otherwise described herein-preferably, the amine group contains two protecting Boc groups to minimize the chance that the single protected amine group would participate in the condensation reaction and substantially reduce the condensation yield)

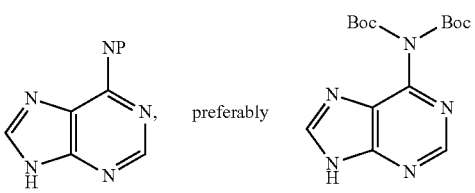

Onto compound 8 in the presence of triphenylphosphine and diisopropylazidocarboxylate (DIAD) in solvent (e.g., THF, DCM) to produce compound 8P or compound 9 where P is at least one amine protecting group (if only one protecting group is present, then the other group is H) or (preferably, P represents two protecting groups, more preferably two BOC groups as represented by compound 9 in FIG. 1, Scheme 1A or FIG. 3, Scheme 2 and as shown below)

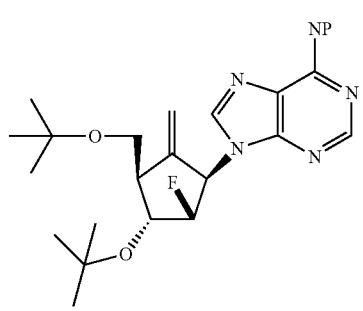

8P

-continued

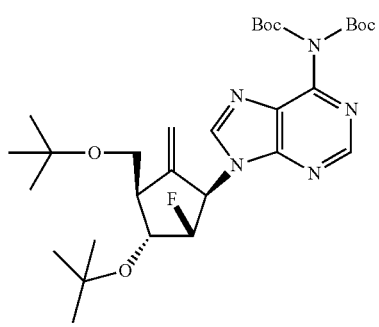
9

Either of which compound is thereafter subjected to deprotection (in the case of the preferred BOC protecting groups, preferably using trifluoroacetic acid/water in solvent to remove both the BOC groups and the ether groups) to produce compound 10 (FMCA),

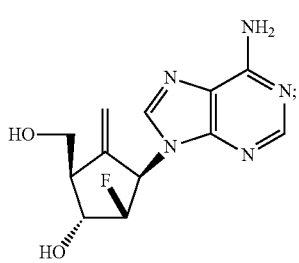
10

FMCA wherein the synthesis may be conducted in a single pot or in steps, with separation and/or purification to produce compounds 8P, compound 9 and/or compound 10 (often using column chromatography/silica gel). Preferably, at least compound 10 is purified as a finished product (for example, using silica gel column chromatography EtOAc/hexane).

In an alternative embodiment, FMCG (compound 11) is prepared from compound 8 by condensing an amine protected 6-chloro purine compound (preferably, the amine protecting group is one or two protecting groups, preferably a BOC group, preferably two BOC groups, but may be other amine protecting groups as otherwise described herein—preferably, the amine group contains two protecting groups to minimize the chance that the single protected amine group would participate in the condensation reaction and substantially reduce the condensation yield. Note that the use of alternative blocking groups, while possible, might increase the number of steps to produce the final product)

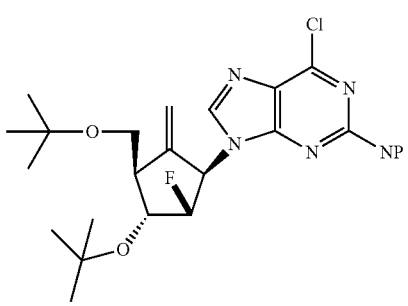

where P represents one or two protecting groups (preferably two BOC groups) onto compound 8 in the presence of triphenylphosphine and diisopropylazidocarboxylate (DIAD) in solvent to produce compound 9P (preferably compound 9G, see FIG. 1, scheme 1A)

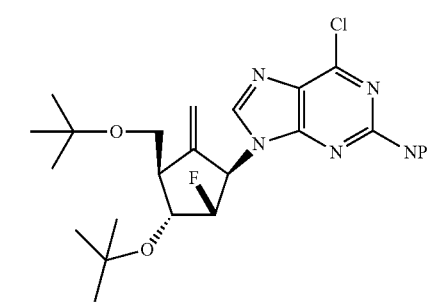
9P

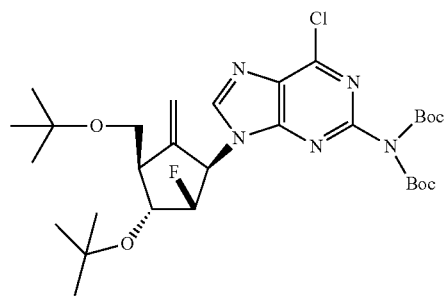
9G where P represents one or two protecting groups (preferably two BOC groups) which are deprotected and the 6-chloro position converted to a keto group (preferably using trifluoroacetic acid/water in solvent) in a single step to produce compound 11 (FMCG),

11

FMCG wherein the synthesis may be conducted in a single pot or in steps, with separation and/or purification to produce compounds 9P, 9G and/or compound 11. Preferably, at least compound 11 is purified as a finished product (column chromatography).

The present invention is also directed to any combination of individual synthetic steps and/or individual compounds (intermediates) along the synthetic scheme. Accordingly, the present invention also is directed to any number of synthetic steps described herein for any of compounds 2, 3, 4, 5, 6, 7, 8, 8P, 9, 9P, 9G, 10 and/or 11 and compound 12 and 12G individually or in any combination. In addition, one or more of the synthetic steps used to provide compounds which are synthesized using methods according to the present invention may be conducted in a single pot or step-wise, by purifying and/or isolating compound after one or more synthetic step.

FMCA (compound 10) and FMCG (compound 11) may each be converted into a phosphoramidate prodrug form by reacting either FMCA or FMCG with an appropriate chlorophenylphosphoryl-L-alaninate reactant (for example, using compound 11A as shown in FIG. 3, Scheme 2 for FMCA or a reagent where the phenyl group is optionally substituted)

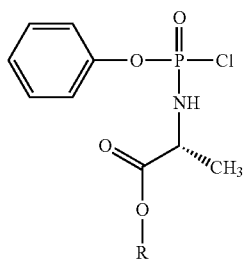

where R is a $C_1$-$C_{20}$ alkyl group, preferably a methyl or isopropyl group (and the phenyl group is optionally substituted) in the presence of methylimidazole or other weak base in solvent (e.g. THF) to produce the 5'-0-phosphoramidate prodrug forms of FMCA and FMCG:

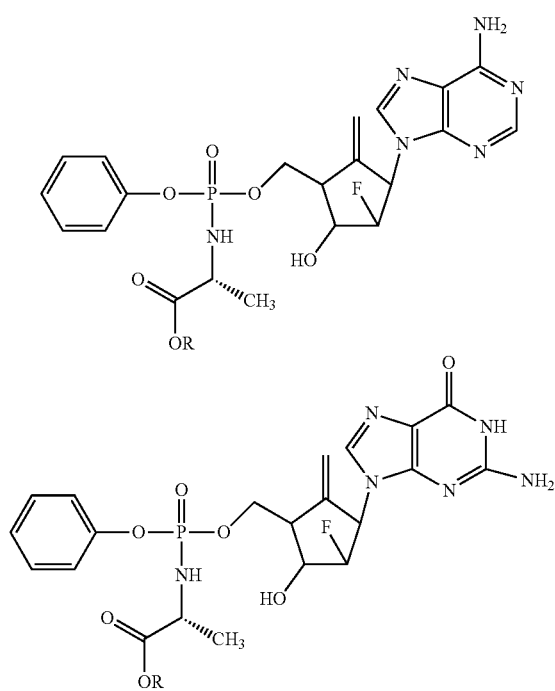

where R is $C_1$-$C_{20}$ alkyl, preferably methyl or isopropyl.

FMCA and FMCG or their prodrug forms are particularly useful as antiviral agents, especially anti-HBV agents.

These and other aspects of the invention are described further in the Detailed Description of the Invention.

DETAILED DESCRIPTION OF THE INVENTION

Figure 1:
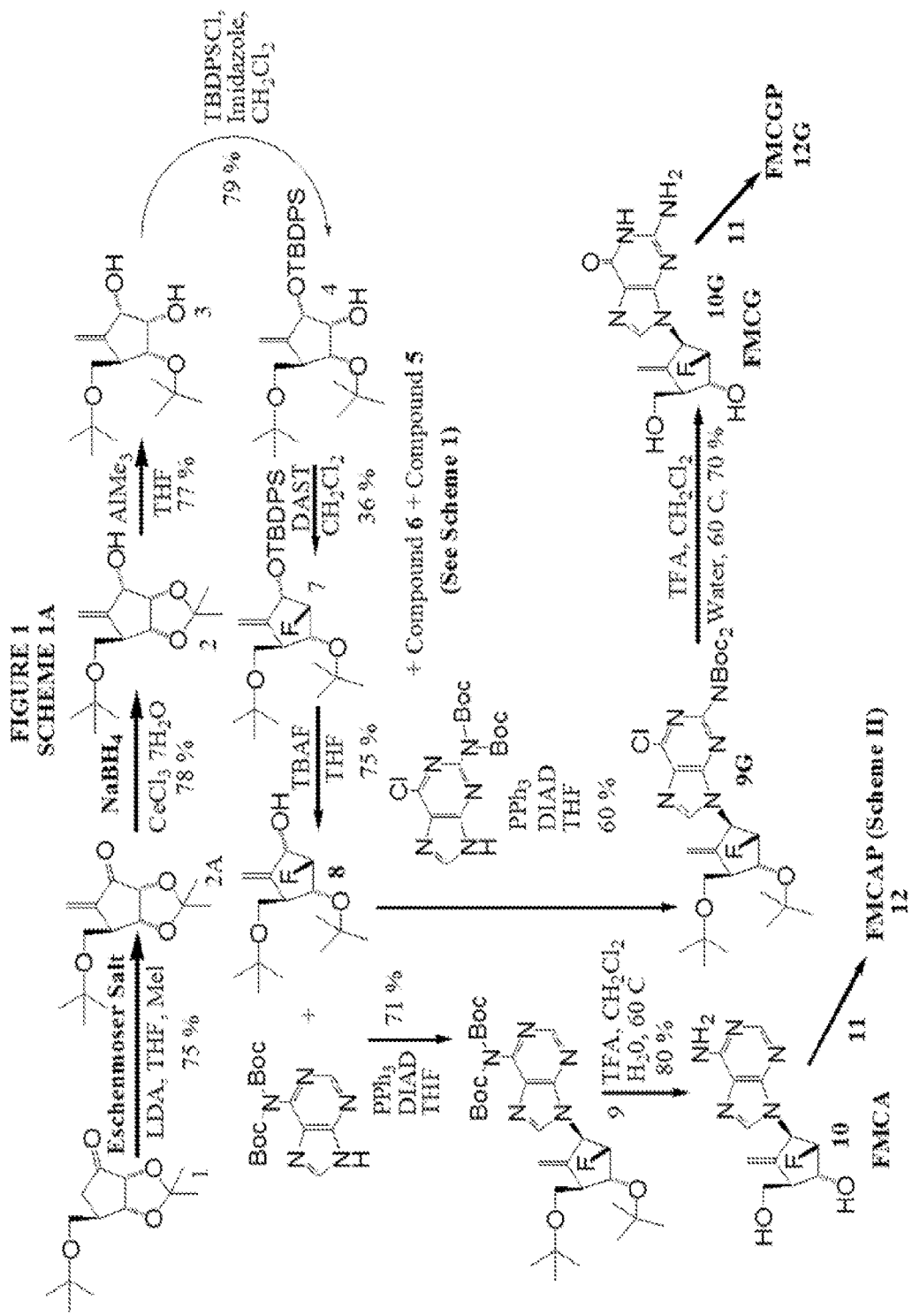
FIG. 1, Scheme 1A shows the synthetic chemical scheme for preparing 2'-fluoro-6'-methylene-carbocyclic adenosine (FMCA) and 2'-fluoro-6'-methylene-carbocyclic guanosine (FMCG) from compound 1 using Eschenmoser salt, strong base (LDA), and methyliodide in solvent.

The following terms are used to describe the present invention. In instances where a term is left undefined, the term is given its art recognized meaning. In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise. The term "about" when used, signifies an amount within ±5% of the amount or number specifically set forth.

The term "compound", as used herein, unless otherwise indicated, refers to any specific chemical compound or intermediate disclosed heroin, and generally refers to β-D nucleoside analogs or intermediates to produce these nucleoside compounds using the synthetic steps described herein, but may include, within context, tautomers, regioisomers, geometric isomers, anomers, and where applicable, optical isomers (enantiomers) or diastereomers (two chiral centers) thereof of these compounds, as well as pharmaceutically acceptable salts thereof, solvates and/or polymorphs thereof. Within its use in context, the term compound generally refers to a single compound, but also may include other compounds such as stereoisomers, regioisomers and/or optical isomers (including racemic mixtures and/or diastereomers as described herein) as well as specific enantiomers, enantiomerically enriched or individual diastereomers or mixtures of disclosed compounds. It is noted that in the event that a carbon range is provided for a compound, that range signifies that each and every carbon individually is considered part of the range. For example a $C_1$-$C_{20}$ group describes a group with a single carbon, two carbon atoms, three carbon atoms, four carbon atoms, etc. up to twenty carbons.

The term "pharmaceutically acceptable salt" or "salt" is used throughout the specification to describe, where applicable, a salt form of one or more of the compounds described herein which are presented to increase the solubility of the compound, in certain embodiments where administration has been effected, in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, ether or amide, phosphoramidate or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical, which may be optionally substituted. It is noted that in the event that a carbon range is provided, that range signifies that each and every carbon is considered part of the range. For example a $C_1$-$C_{20}$ group describes a group with a single carbon, two carbon atoms, three carbon atoms, four carbon atoms, etc. The term "ether" shall mean an optionally substituted $C_1$ to $C_{20}$ ether group, formed from an oxygen and an alkyl group, or alternatively, may also contain at least one oxygen within the alkyl or alkylene chain.

The term "aromatic" or "aryl" shall mean within its context a substituted or unsubstituted monovalent carbocyclic aromatic radical having a single ring (e.g., phenyl) or multiple condensed rings (e.g., naphthyl, anthracene, phenanthrene). Other examples include optionally substituted heterocyclic aromatic ring groups ("heteroaromatic" or "heteroaryl") having one or more nitrogen, oxygen, or sulfur atoms in the ring, and preferably include five or six-membered heteroaryl groups, such as imidazole, furyl, pyrrole, furanyl, thiene, thiazole, pyridine, pyrazine, triazole, oxazole, among others, but can also include fused ring heteroaryl groups such as indole groups, among others. The preferred aryl group in compounds according to the present invention is a phenyl or a substituted phenyl group.

The term "heterocycle" shall mean an optionally substituted moiety which is cyclic and contains at least one atom other than a carbon atom, such as a nitrogen, sulfur, oxygen or other atom, which ring may be saturated and/or unsaturated.

The term "unsubstituted" shall mean substituted only with hydrogen atoms. The term "substituted" shall mean, within the chemical context of the compound defined, a substituent (each of which substituent may itself be substituted) selected from a hydrocarbyl (which may be substituted itself, preferably with an optionally substituted alkyl or fluoro group, among others), preferably an alkyl (generally, no greater than about 3 carbon units in length), including $CF_3$, an optionally substituted aryl, halogen (F, Cl, Br, I), thiol, hydroxyl, carboxyl, $C_1$-$C_3$ alkoxy, alkoxycarbonyl, CN, nitro or an optionally substituted amine (e.g., an alkyleneamine or a $C_1$-$C_3$ monoalkyl or dialkyl amine). Various optionally substituted moieties may be substituted with 3 or more substituents, preferably no more than 3 substituents and preferably with 1 or 2 substituents.

The term "acyl" is used throughout the specification to describe a group at the 5' or 3' position of the nucleoside analog (i.e., at the free hydroxyl position in the carbocyclic moiety) or on the exocyclic amine of the nucleoside base which contains a $C_1$ to $C_{20}$ linear, branched or cyclic alkyl chain. The acyl group in combination with the hydroxyl group results in an ester and the acyl group in combination with an exocyclic amine group results in an amide, which, after administration, may be cleaved to produce the free nucleoside form of the present invention. Acyl groups according to the present invention are represented by the structure:

where $R^4$ is a $C_1$ to $C_{20}$ linear, branched or cyclic alkyl group which is optionally substituted preferably with, for example, 1-3 hydroxyl groups, 1-3 halo groups (F, Cl, Br, I) or an amine group (which itself may be optionally substituted with one or two $C_1$-$C_6$ alkyl groups optionally bearing between 1 and 3 hydroxyl groups), alkoxyalkyl (including an ethylene oxide chain which may end in a free hydroxyl group or a $C_1$-$C_{10}$ alkyl group and ranges in molecular weight from about 50 to about 40,000 or about 200 to about 5,000), such as phenoxymethyl, aryl, alkoxy, alkoxycarbonyloxy groups (e.g., [(isopropoxycarbonyl)oxy]-methoxy), aryloxyalkyl, among others, all of which groups may be optionally substituted, as described above. Preferred acyl groups are those where $R^4$ is a $C_1$ to $C_{12}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others and may include such related groups as sulfone groups such as mesylate groups. All groups may be appropriately substituted within context as otherwise described herein. One of ordinary skill in the art will recognize the acyl groups which will have utility in the present invention, either to synthesize the target pharmaceutical compounds or as prodrug of the nucleosides according to the present invention.

The term "amino acid" or "amino acid residue" shall mean, within context, a radical of a D- or L-amino acid which is covalently bound to a nucleoside analog at the 4' exocyclic amine position of the cytosine base or the 5'- or 3'-OH position of the sugar synthon ($R^2$, $R^1$ or $R^{1a}$) through a carboxylic acid moiety of the amino acid, thus forming respectively, an amide or ester group linking the nucleoside to the amino acid. Amino acids may also be used to provide phosphoamidate groups in nucleoside compounds according to the present invention as otherwise described herein. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "phosphate ester" or "phosphodiester" (which term includes phosphotriester groups and phosphoamidate groups in context) is used throughout the specification to describe mono-phosphate groups at the 5' position of the carboyclic sugar synthon which are mono- or diesterified (or amidated and optionally esterified in the case of a phosphoamidate) such that the phosphate group is negatively charged or is rendered neutral, i.e., has a neutral charge. Phosphate esters, phosphodiesters and/or phosphoamidate groups for use in the present invention include those represented by the structures:

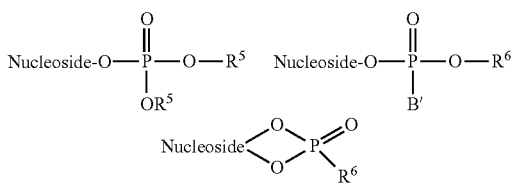

where each $R^5$ and $R^6$ is independently selected from H, a $C_1$ to $C_{20}$ linear, branched or cyclic alkyl group, alkoxyalkyl, aryloxyalkyl, such as phenoxymethyl, optionally substituted aryl (especially an optionally substituted phenyl group) and alkoxy, among others, including alkoxycarbonyloxy groups (e.g., (isoptopoxycarbonyl)oxy]-methoxy) each of which groups may be optionally substituted (e.g., a phenyl or other group may be optionally substituted as otherwise described herein or preferably with from one to three, $C_1$-$C_6$ alkyl groups, halogen, preferably F, Cl or Br, nitro, cyano, or $C_2$-$C_6$ carboxyester groups) with the proviso that at least one $R^5$ group is other than H, or the two $R^5$ groups together form a five- or six-membered heterocyclic group;

B' is a

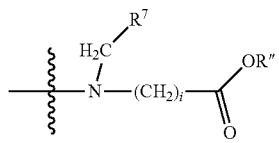

group or a group obtained from an amino acid (a natural or unnatural amino acid such as, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others) to preferably provide a group according to the structure

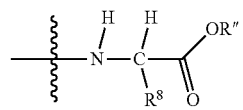

where i is 0, 1, 2 or 3 (preferably 0)

$R^7$ is a $C_1$ to $C_{20}$ linear, branched or cyclic alkyl or acyl group, alkoxyalkyl, aryloxyalkyl, such as phenoxymethyl, optionally substituted aryl group (as described above) and alkoxy among others, each of which groups may be optionally substituted;

$R^8$ is sidechain of an amino acid, preferably a sidechain of an amino acid selected from the group consisting of alanine, β-alanine, arginine, asparagine, aspartic acid, cysteine, cystine, glutamic acid, glutamine, glycine, phenylalanine, histidine, isoleucine, lysine, lencine, methionine, proline, serine, threonine, valine, tryptophan or tyrosine (preferably $R^8$ is derived from alanine, leucine, isoleucine or threonine, more preferably alanine-$R^8$ is methyl), and R" is a $C_1$ to $C_{20}$ linear, branched or cyclic alkyl or a phenyl or heteroaryl group, each of which groups is optionally substituted.

Preferred monophosphate esters for use in prodrug forms according to the present invention are those where $R^5$ is a $C_1$ to $C_{20}$ linear or branched chain alkyl group, more preferably a $C_1$ to $C_3$ alkyl group, all of which groups may be optionally substituted. Other compounds which are preferred are as otherwise set forth herein, especially, where $R^1$ is a phosphoamidate group as otherwise described herein. A preferred phosphoamidate is

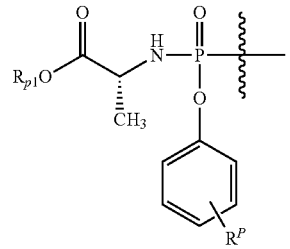

where $R_{p1}$ is an optionally substituted (OH, halo) $C_1$-$C_{20}$ alkyl group, preferably a $C_1$-$C_4$ alkyl group, even more preferably a methyl, ethyl, isopropyl group or isobutyl group; and $R^P$ is H, nitro, cyano, methoxy, or a $C_1$-$C_3$ alkyl group optionally substituted with from 1-3 halogen substituents (preferably F).

Preferred phosphoamidate groups for $R^1$ include those according to the chemical structure:

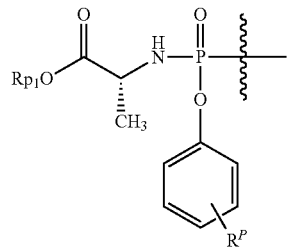

where $R^P$ is H or $C_1$-$C_3$ alkyl group (preferably H) and $R_{p1}$ is methyl, ethyl, isopropyl or isobutyl group, more preferably a methyl or isopropyl group.

In other embodiments R¹ is a

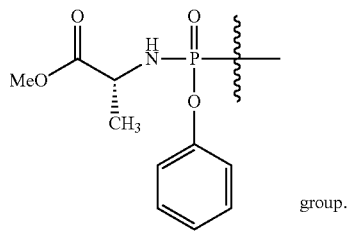 [SMILES: *P(=O)(N[C@H](C)C(=O)OC)Oc1ccccc1]

group.

The term "effective amount" shall mean an amount or concentration of a compound according to the present invention which is effective within the context of its administration or use, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit the growth, reduce the likelihood of or treat viral infections in patients as otherwise described herein.

The term "D-configuration" as used in the context of the present invention refers to the configuration of the nucleoside compounds according to the present invention which mimics the natural configuration of sugar moeties as opposed to the unnatural occurring nucleosides or "L" configuration. The term "β" or "β anomer" is used to describe nucleoside analogs according to the present invention in which the nucleoside base is configured (disposed) above the plane of the carbocyclic moiety in the compound.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Carbocyclic nucleoside compounds according to the present invention are generally β-D-nucleoside compounds. When the present compounds according to the present invention are referred to in this specification, it is presumed that the nucleosides have the D-nucleoside configuration and are enantiomerically enriched (preferably, about 100% of the D-nucleoside), unless otherwise stated. The term "diasteronterically pure" is used to describe a single diastereomer of a compound according to the present invention which contains at least 95%, 96%, 97%, 98%, 99%, 99.5% or 100% by weight of a single diastereomer to the exclusion of other possible diastereomers.

The term "stereoselective" is used to describe a synthetic step or series of steps in which a single reactant produces a particular isomer (of at least two possible isomers) in greater quantities than one or more possible isomer(s) from that reactant. In some instances the stereoselectivity of a reaction may be close to 100%.

The term "protecting group" or "blocking group" is used to describe a chemical group or moiety which is introduced into a molecule by chemical modification of a functional group to obtain chemoselectivity in a subsequent chemical reaction. It plays an important role in providing precursors to chemical components which provide compounds according to the present invention. Blocking groups may be used to protect hydroxyl groups on the sugar synthon or the purine based in order to form compounds according to the present invention. Typical blocking groups are used on alcohol groups and amine groups in the present invention.

Exemplary alcohol/hydroxyl protecting groups include acetyl (removed by acid or base), benzoyl (removed by acid or base), benzyl (removed by hydrogenolysis, β-methoxyethoxymethyl ether (MEM, removed by acid), dimethoxytrityl [bis-(4-methoxyphenyl)phenylmethyl] (DMT, removed by weak acid), methoxymethyl ether (MOM, removed by acid), methoxytrityl [(4-methoxyphenyl)diphenylmethyl], (MMT, Removed by acid and hydrogenolysis), p-methoxylbenzyl ether (PMB, removed by acid, hydrogenolysis, or oxidation), isopropylidene (removed by acid), methylthiomethyl ether (removed by acid), pivaloyl (Piv, removed by acid, base or reductant agents. More stable than other acyl protecting groups, tetrahydropyranyl (THP, removed by acid), tetrahydrofuran (THF, removed by acid), trityl (triphenyl methyl, (Tr, removed by acid), silyl ether (e.g. trimethylsilyl, TMS, tert-butyldimethylsilyl or TBDMS, tri-isopropylsilyloxymethyl or TOM, triisopropylsilyl or TIPS, and t-buyldiphenylsilyl, all removed by acid or fluoride ion such as such as NaF, TBAF (tetra-n-butylammonium fluoride, HF-Py, or HF-NEt₃); alkyl ethers, including methyl or t-butyl ether (removed by strong acid, TMSI in DCM, MeCN or chloroform or by BBr₃ in DCM) or ethoxyethyl ethers (removed by strong acid). In preferred aspects of the present invention, the use of a t-butyl ether is often preferred. In preferred aspects, the hydroxyl protecting groups used in the sugar synthon are t-butyl ether, isopropylidene and t-butyldiphenylsilyl protecting groups as otherwise disclosed herein.

Exemplary amine-protecting groups include carbobenzyloxy (Cbz group, removed by hydrogenolysis), p-Methoxylbenzyl carbon (Moz or MeOZ group, removed by hydrogenolysis), tert-butyloxycarbonyl (BOC group, removed by concentrated strong acid or by heating at elevated temperatures), 9-Fluorenylmethyloxycarbonyl (FMOC group, removed by weak base, such as piperidine or pyridine), acyl group (acetyl, benzoyl, pivaloyl, by treatment with base), benzyl (Bn groups, removed by hydrogenolysis), carbamate, removed by acid and mild heating, p-methoxybenzyl (PMB, removed by hydrogenolysis), 3,4-dimethoxbenzyl (DMPM, removed by hydrogenolysis), p-methoxyphenyl (PMP group, removed by ammonium cerium IV nitrate or CAN); tosyl (Ts group removed by concentrated acid and reducing agents, other sulfonamides, Mesyl, Nosyl & Nps groups, removed by samarium iodide, tributyl tin hydride. In preferred aspects of the present invention, two BOC groups are used to protect the exocyclic purine (adenine or guanine) amine which is condensed with the sugar synthon to produce FMCA and FMCG pursuant to the present invention. In preferred aspects the hydroxyl protecting groups used in the sugar synthon are t-butyl ether, isopropylidene and t-butyldiphenylsilyl protecting groups as otherwise disclosed herein.

Chemical Synthesis

Preferred Synthesis of Intermediate 8

In one embodiment, the invention provides a process for synthesizing a compound of formula 8:

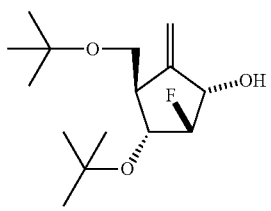

From substituted pentanone derivative 1:

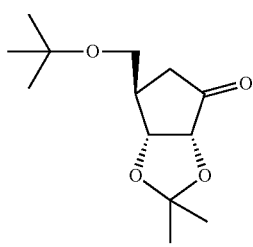

Comprising introducing a methylene group in a position α to the keto group of compound 1 by reacting compound 1 with a strong base (e.g. LDA or other strong base) in solvent at low temperature (e.g., −78° C.) followed by the addition of Eschenmoser Salt to produce a mixture which is stirred for several hours (about 2-4 hours, preferably 3 hours) at low temperature following by a longer period (e.g. 4-10 hours or longer) at room temperature at which time iodomethane is added and stirred at ambient temperature (preferably, room temperature) for a period of about 4-6 hours, preferably about 4 hours and the solution was quenched with weak base (e.g., 10% aqueous sodium bicarbonate, extracted (organic solvent, preferably methylene chloride) and washed and optionally purified (e.g., silica gel column, flash silica) to provide compound 2A below:

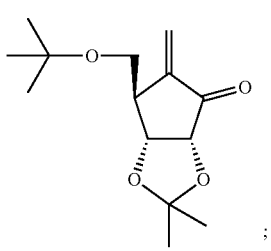

Compound 2 is prepared from compound 2A by reducing the keto group by dissolving compound 2A in solvent (e.g. anhydrous methanol) at low temperature (−78° C.), adding CeCl₃ or other Lewis acid, stirring for a short period followed by the addition of sodium borohydride, stirring for a further period (e.g. about 30 minutes to one hour), and allowing the solution to increase in temperature to about 0° C. whereupon ammonium chloride was added and stirred for an additional hour before solvent was removed (preferably under reduced pressure) and the residue obtained was extracted with solvent (e.g., methylene chloride), the combined organic extracts combined, washed (e.g., with brine), dried and concentrated under vacuum before being further purified (e.g. silica gel column or flash silica) to produce compound 2, below Alternatively and preferably to produce compound 2 in two steps (preferably without purification), compound 1 is treated with paraformaldehyde (HCHO)₄ in the presence of diisopropyl ammonium trifluoracetate salt and diisopropylamine in solvent (e.g. THF) at elevated temperature (preferably, reflux) to introduce a double bond (an olefin group) at position 6 in compound 1 to provide compound 2A in high yield (at least 60% from compound 1, more often at least 70% from compound 1), which is optionally purified by chromatography (e.g. silica gel column 5% EtOAc/hexane) and is subsequently reduced in situ (preferably, without further purification) using a reducing agent (e.g. sodium borohydride) and a Lewis acid (e.g., CeCl₃.7H₂O) in solvent (e.g. methanol. Preferably, the keto group of compound 2A is stereoselectively reduced using sodium borohydride in the presence of CeCl₃ in solvent (e.g., DCM) at reduced temperature to produce compound 2

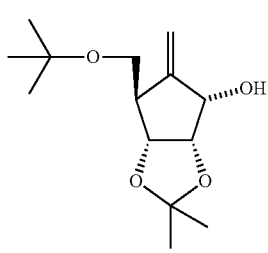

which is optionally and preferably isolated (e.g. silica gel column chromatography) in high yield in a single pot over two steps (at least about 50%, preferably 52% or more);

Compound 2 is then reacted with AlMe3 in solvent (e.g. THF or other solvent) at ambient temperature followed by quenching with an alcohol (methanol)/ammonium chloride solution at low temperature (e.g. about −20° C. to −50° C., preferably −30° C.) and purified (e.g., column chromatography, other) to produce compound 3, below

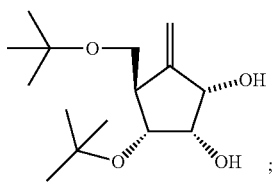

Compound 3 is then reacted with a silyl protecting group reagent (preferably, a sterically hindered silyl group reagent such as tert-butyldiphenylsilyl chloride) in a solvent (e.g. anhydrous methylene chloride) containing a base to scavenge HCl acid (e.g. imidazole) at low temperature (e.g. 0° C.) for a period of time to selectively protect the less hindered hydroxyl group, of compound 3, which is then separated (e.g. by diluting the reaction mixture with water and separating out the organic layer with drying) and then purifying the organic layer (e.g. column chromatography, other separation techniques) to produce compound 4, below

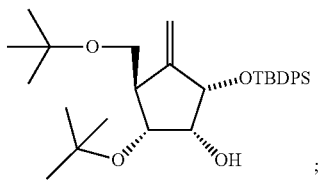

Compound 4 is then reacted with a fluorinating agent (e.g. diethylaminosulfur trifluoride DAST) in anhydrous solvent (e.g. methylene chloride) to stereoselectively fluorinate the 2' position, quenched (ice water at −20° C.), the organic layer separated, extracted (e.g. methylene chloride) and purified to produce compound 7, below (compounds 5 and 6 of FIG. 2, Scheme 1 are also produced during the reaction)

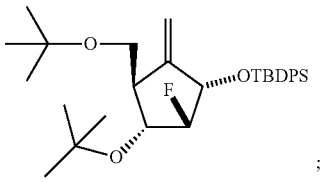

Compound 8 is then reacted to remove the silyl protecting group (preferably using tetrabutylammonium fluoride) in (solvent) THF, separated, collected and purified to provide compound 8 below:

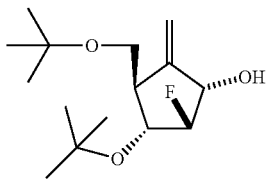

Synthesis of FMCA from Compound 8

FMCA is synthesized in two steps in high yield from Compound 8

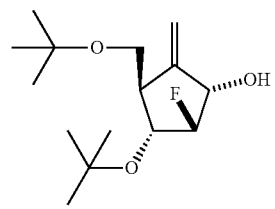

by reacting compound 8 with a preferred protected adenine derivative according to the chemical structure:

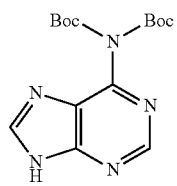 [SMILES: CC(C)(C)OC(=O)N(C(=O)OC(C)(C)C)c1ncnc2[nH]cnc12]

wherein triphenylphosphine and diisopropylazidocarboxylate (DIAD) are mixed in solvent (preferably, THF) at reduced temperature (e.g. about −10° C.) for a period of about 20-45 minutes and the protected adenine derivative is added and mixed at reduced temperature (e.g. 0° C.) for a further period of time (e.g. 20-45 minutes, preferably about 30 minutes) after which time compound 8 is added and stirred for a sufficient period (e.g. about 1.5 hours) to couple the protected adenine compound to sugar synthon (compound 8) to produce compound 9, below after purification (column chromatography)

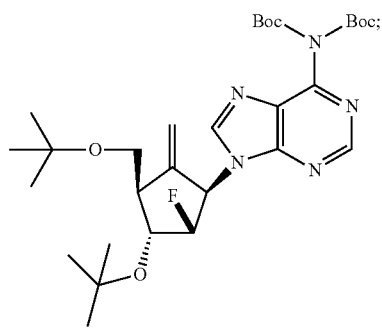

Compound 9 is de-protected (preferably using trifluoroacetic acid in water, at about 60° C. for a sufficient time to remove the protecting groups—about 2 hours or so) and purified to provide compound 10 (FMCA):

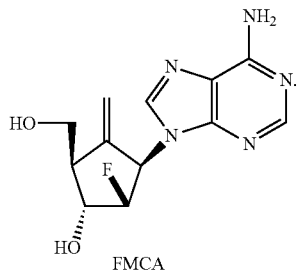

FMCA

Synthesis of FMCG from Compound 8

FMCG is synthesized in two steps in high yield from Compound 8

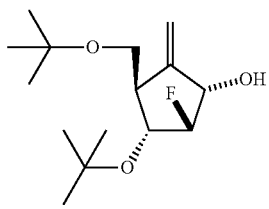

by reacting compound 8 with a 2-amino protected 6-chloro purine derivative according to the preferred chemical structure:

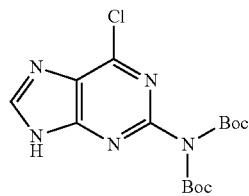 [SMILES: CC(C)(C)OC(=O)N(C(=O)OC(C)(C)C)c1nc(Cl)c2nc[nH]c2n1]

wherein triphenylphosphine and diisopropylazidocarboxylate (DIAD) are mixed in solvent (preferably, THF) at reduced temperature (e.g. about −10° C.) for a period of about 20-45 minutes is mixed and the protected adenine derivative is added and mixed at reduced temperature (e.g. 0° C.) for a further period of time (e.g. 20-45 minutes, preferably about 30 minutes) after which time compound 7 is added and stirred for a sufficient period (e.g. about 1.5 hours) to couple the protected 6-chloropurine compound to the sugar synthon (compound 7) to produce compound 9G, below after purification (column chromatography)

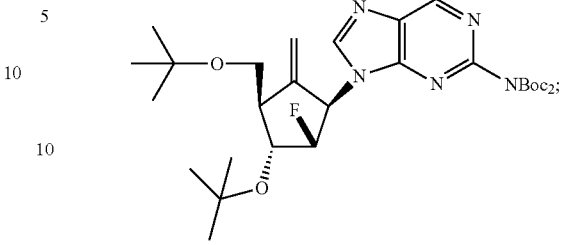

Compound 9G is de-protected and the 6-chloro position is converted to a keto group using trifluoroacetic acid in water (preferably at about 60° C. for a sufficient time to remove the protecting groups—about 2 hours or so) and purified to provide compound 11 (FMCG):

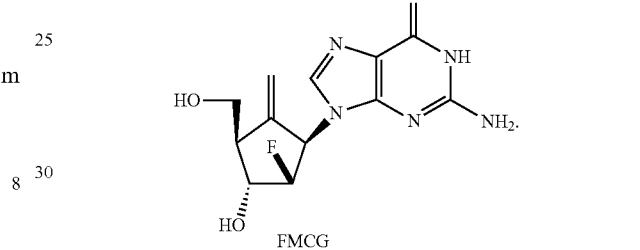

FMCG

The experiment section which details the chemical synthesis of FMCA (compound 10) and FMCG (compound 11) is set forth in detail below.

EXAMPLES

First Set of Examples (Associated With FIG. 1, Scheme 1A)

(3aR,6R,6aR)-6-(tert-butoxymethyl)-2,2-dimethyl-5-methylenedihydro-3aH-cyclopenta[d][1,3]dioxol-4(5H)-one (2A)

To a stirred solution of 1 (15 g, 61.9 mmol) in THF at −78 C was added LDA solution in THF (53.6 ml, 80 mmol) using a dropping funnel. This solution was stirred for 3 h at −78 C and Eshenmoser's salt (45.8 g, 248 mmol) was added in one portion. The mixture was stirred for additional 3 h at the same temperature and 8 h at room temperature. Then iodomethane (131 mL) was added and stirred for another 4 h at room temperature. The mixture was quenched with 10% aqueous $NaHCO_3$ (100 mL) and stirred for 1 h and extracted with methylene chloride (2×300 mL). The combined organic extracts were washed with 10% aqueous $NaHCO_3$ (200 mL) followed by brine (80 mL) and dried ($Na_2SO_4$) and concentrated in vacuum. The residue was purified over flash silica (5% EtOAc/hexane) to give compound 2 as light yellow oil. Yield (11.4 g. 72.4%); $^1$H NMR [500 MHz, $CDCl_3$]: δ 6.22 (d, J=2 Hz, 1H), 5.52 (d, J=1.5 Hz, 1H), 4.59 (d, J=5 Hz, 1H), 4.48 (d, J=4.5 Hz, 1H), 3.64 (dd, J=3.5, 8.5 Hz, 1H), 3.46 (dd, J=3.5, 8.5 Hz, 1H), 3.09 (m, 1H), 1.37 (s, 3H), 1.35 (s, 3H), 1.08 (s, 9H);

MS (ESI) m/z: 255 [M+H]$^+$

(3aS,4S,6R,6aR)-6-(tert-butoxymethyl)-2,2-dimethyl-5-methylenetetrahydro-3aH-cyclopenta[d][1,3]dioxol-4-ol (2)

To a solution of compound 2 (11.4 g, 44.8 mmol) in anhydrous methanol (150 mL) was added CeCl$_3$.7H$_2$O (18.37 g, 49.3 mmol) at −78 C and stirred for 10 minutes. NaBH$_4$ (1.86 g, 49.3 mmol) was then added to this mixture in one portion. After 30 min the reaction mixture was allowed to come to 0 C and saturated NH$_4$Cl (20 was added. It was stirred for an additional hour and then solvent was removed under reduced pressure. The residue was extracted with methylene chloride (2×200 mL). The combined organic extracts were washed with brine, dried (Na$_2$SO$_4$) and concentrated under vacuum. The residue thus obtained was purified over flash silica (5% EtOAc/hexane) to obtain 3 as a white solid. Yield (9.1 g, 79%); $^1$H NMR [500 MHz, CDCl$_3$]: δ 5.25 (s, 1H), 5.11 (s, 1H), 4.50-4.53 (m, 3H), 3.46 (dd, J=3.5, 8.5 Hz, 1H), 3.27 (dd, J=3.5, 8.5 Hz, 1H), 2.63 (t, J=3.5 Hz, 1H), 2.25 (d, J=11 Hz, 1H) 1.40 (s, 3H), 1.34 (s, 3H), 1.12 (s, 9H);
MS (ESI) m/z: 251 [M+H]$^+$

(1S,2S,3R,4R)-3-tert-butoxy-4-(tert-butoxymethyl)-5-methylenecyclopetane-1,2-diol (3)

Compound 3 (2.2 g, 8.58 mmol) was dissolved in 20 ml of THF and cooled to 0 C on an ice bath followed by the addition of Trimethylaluminium solution (172 mmol, 86 ml). This reaction was stirred at ambient temperature for 72 h. Reaction was then cooled to −30 C and quenched with 2 ml of methanol and saturated ammonium chloride solution. Column chromatography using ethyl acetate and hexane as eluent afforded 3 as off white solid. Yield (1.8 g, 77%). $^1$H-NMR [500 MHz, CDCl$_3$] δ 5.32 (s, 1H), 5.11 (s, 1H), 4.24 (s, 1H), 4.07-4.05 (m, 1H), 3.94-3.92 (m, 1H), 3.44 (dd, J=4.5 & 8.5 Hz, 1H), 3.35 (dd, J=5.0 & 8.5 Hz, 1H), 2.80 (bs, 1H). 2.64-2.62 (m, 1H), 2.51 (bs, 1H), 1.25 (s, 9H), 1.15 (s, 9H)
MS (ESI) m/z: 258 [M+H]$^+$

(1R,2R,3R,5S)-2-tert-butoxy-3-(tert-butoxymethyl)-5-(tert-butyldiphenylsilyloxy)-4-methylenecyclopentanol (4)

In a solution of compound 4 (1.7 6.24 mmol g, mmol) in anhydrous methylene chloride (25 ml) at 0 C was added imidazole (0.85 g, 12.48 mmol) and stirred for 5 minutes. To this solution was added tert-butyldiphenylsilyl chloride (2.06 g, 7.49 mmol) and the mixture was stirred for 2 h. Reaction mixture was diluted with water (20 ml) and organic layer was separated, washed with water (2×20 ml) and dried over sodium sulfate. Organic layer was dried under vacuum to obtain crude product which was purified by column chromatography (ethyl acetate: hexane, 1:9) to give 5 as oil. Yield: (2.52 g, 79%); $^1$H-NMR [500 MHz, CDCl$_3$] δ 7.80-7.78 (m, 2H), 7.74-7.71 (m, 3H), 7.43-7.35 (m, 5H), 5.19 (s, 1H), 5.00 (s, 1H), 4.36 (s, 1H), 3.82-3.79 (m, 1H), 3.56 (s, 1H), 3.36-3.33 (m, 2H), 2.70 (d, J=2.0 Hz, 1H), 2.57 (s, 1H), 1.13 (s, 9H), 1.10 (s, 9H), 1.05 (s, 9H);
MS (ESI) m/z: 512 [M+H]$^+$

((1S,3R,4R)-3-tert-butoxy-4-(tert-butoxymethyl)-2-fluoro-5-methylenecyclopentyloxy)(tert-butyl)diphenylsilane (7)

To a solution of compound 5 (2.5 g, 4.89 mmol) in anhydrous dichloromethane (DCM) was added diethylaminosulfur trifluoride (DAST; 3.23 mL, 24.47 mmol) slowly at −20° C., and the mixture was warmed to room temperature with stirring for 30 min. The reaction mixture was quenched with ice-water at −20° C., the organic layer was collected, and the aqueous phase was extracted with DCM (20 mL×2). The combined organic layers were dried over Na$_2$SO$_4$, and the solvent was removed under reduced pressure. The crude residue was purified by flash silica gel column chromatography (1% EtOAc/99% hexane) to give 7 as yellowish oil. Yield: (900 mg, 36%); $^1$H-NMR [500 MHz, CDCl$_3$] δ 7.75-7.73 (m, 4H), 7.45-7.37 (m, 6H), 5.11 (s, 1H), 4.94 (s, 1H), 4.74-4.71 (m, 0.5H), 4.64-4.60 (m, 1.5H), 4.03-3.97 (m, 1H), 3.42 (dd, J=4.0 & 8.0 Hz, 1H), 3.32 (dd, J=4.0 & 8.5 Hz, 1H), 2.50 (s, 1H), 1.14 (s, 9H), 1.12 (s, 9H), 1.08 (s, 9H); $^{19}$F-NMR [500 MHz, CDCl$_3$]: δ−188.98 (s, 1F);
MS (ESI) m/z: 514 [M+H]$^+$

(1S,3R,4R)-3-tert-butoxy-4-(tert-butoxymethyl)-2-fluoro-5-methylenecyclopentanol (8)

To a solution of compound 7 (0.9 g, 1.80 mmol) in THF was added tetrabutylammonium fluoride (TBAF, 1 M solution in THF) (3.61 mL, 3.61 mmol), and this mixture was stirred at room temperature for 3 h. The solvent was removed under reduced pressure; the residue was taken in ethylacetate (50 mL) and washed with water (2×20 mL). The organic layer was collected, dried (Na$_2$SO$_4$), filtered, and concentrated under reduced pressure. The residue was purified by column chromatography on silica gel using ethyl acetate in hexane as eluent to afford 8 as a foam. Yield (0.35 g, 75% $^1$H-NMR [500 MHz, CDCl$_3$] δ 5.33 (s, 1H), 5.16 (d, J=2.5 Hz, 1H), 4.64-4.62 (m, 0.5H), 4.54-4.47 (m, 1.5H), 4.21-4.16 (m, 1H), 3.50-3.48 (m, 1H), 3.43-3.40 (m, 1H), 2.64 (d, J=2.5 Hz, 1H), 2.28 (d, J=8.0 Hz, 1H) 1.26 (s, 9H), 1.19 (s, 9H); $^{19}$F-NMR [500 MHz, CDCl$_3$]: δ−189.2 (s, 1F);
MS (ESI) m/z: 275 [M+H]$^+$;

9-((1R,3R,4R)-3-tert-butoxy-4-(tert-butoxymethyl)-2-fluoro-5-methylenecyclopentyl)-N,N-diboc-9H-purin-6-amine (9)

To a stirred solution of triphenylphosphine (115 mg, 0.44 mmol), in THF (15 mL) at −10° C., DIAD was added (88 mg, 0.44 mmol) dropwise, the reaction mixture was stirred at this temperature for 30 min, and then solution of N,N-diBoc-protected adenine (110 mg, 0.33 mmol) in THF (2 mL) was added; this mixture was stirred for 30 min at 0° C. Compound 7 (60 mg, 0.22 mmol) in THF (1 mL) was then added, and the reaction mixture was stirred for 1.5 h at room temperature. The solvent was removed under reduced pressure, and the residue was purified by silica gel column chromatography (EtOAc/hexane 1/20 to 1/10) to give 9 as white foam. Yield (95 mg, 60%); $^1$H-NMR [500 MHz, CDCl$_3$] δ 8.92 (s, 1H), 8.25 (s, 1H), 5.98 (d, J=28.5 Hz, 1H), 5.32 (s, 1H), 4.92 (s, 0.5H), 4.81-4.72 (m, 1.5H), 4.34 (d, J=14 Hz, 1H), 3.64-3.61 (m, 1H), 3.56-3.52 (m, 1H), 2.87 (m, 1H), 1.48 (s, 18H), 1.29 (s, 9H), 1.28 (s, 9H): $^{19}$F-NMR [500 MHz, CDCl$_3$]: δ−188.14 (s, 1F); MS (ESI) m/z: 421 [M+H]$^+$;

(1R,3R,5R)-3-(6-amino-9H-purin-9-yl)-2-fluoro-5-(hydroxymethyl)-4-methylenecyclopentanol (FMCA, 10)

Compound 9 (80 mg, 0.116 mmol) was dissolved in a mixture of trifluoroacetic acid and water (5 mL, 3:2), and the mixture was stirred at 60 C for 2 h. The solvent was removed under reduced pressure and the residue was purified by column chromatography on silica gel (methanol/DCM 0.2/10 to 0.6/10) to give 9 (26 mg, 80%) as a white solid: mp 215-218° C.; [α] 25D=+152.10° (c 0.5, MeOH); $^1$H-NMR [500 MHz, CD$_3$OD]: δ 8.26 (s, 1H), 8.10 (d, J=2.5 Hz, 1H), 5.90 (d, J=25.0 Hz, 1H), 5.46 (s, 1H), 4.96 (dt, J=2.5, 52.5 Hz, 1H), 4.95 (s, 1H), 4.44 (dt, J=3.0, 14.0 Hz, 1H), 3.81-3.91 (m, 2H), 2.81 (s, 1H); 19F NMR (500 MHz, DMSO-d6) δ−192.93 (ddd, J=14.0, 28.0, and 56.0 Hz, 1F); 13C{1H} NMR [125 MHz, CD$_3$OD]: δ 51.0, 57.5 (d, J=17.4 Hz), 61.7, 72.9 (d, J=23.6 Hz), 95.9 (d, J=184.0 Hz), 111.7, 117.9, 141.1, (d, J=5.3 Hz), 146.0, 149.9, 152.5, 156.0.

9-((1R,2R,3R,4R)-3-tert-butoxy-4-(tert-butoxymethyl)-2-fluoro-5-methylenecyclopentyl)-6-chloro-N,N-diboc-9H-purin-2-amine (9G)

To a stirred solution of triphenylphosphine (86 mg, 0.33 mmol), in THF (15 mL) at −10° C., DIAD was added (67 mg, 0.33 mmol) dropwise, the reaction mixture was stirred at this temperature for 30 min, and then a solution of 2-N,N-diBoc-protected-6-Cl-purine (121 mg, 0.33 mmol) in THF (2 mL) was added; this mixture was stirred for 30 min at 0° C. Compound 7 (60 mg, 0.22 mmol) in THF (1 mL) was then added, and the reaction mixture was stirred for 1.5 h at room temperature. The solvent was removed under reduced pressure, and the residue was purified by silica gel column chromatography (EtOAc/hexane 1/20 to 1/10) to give 9G as white foam. Yield (95 mg, 60%); $^1$H-NMR [500 MHz, CDCl$_3$]δ 8.35 (s, 1H), 5.87 (d, J=25 Hz, 1H), 5.37 (s, 1H), 4.92 (s, 0.5H), 4.88 (s, 1.5H), 4.78 (s, 0.5H) 4.34 (d, J=13.5 Hz, 1H), 3.64-3.62 (m, 1H), 3.57-3.54 (m, 1H), 2.84 (m, 1H), 1.48 (s, 18H), 1.28 (s, 18H); $^{19}$F-NMR [500 MHz, CDCl$_3$]: δ−187.12 (s, 1F); MS (ESI) m/z: 627 [M+H]$^+$;

2-amino-9-((1R,2R,3R,4R)-2-fluoro-3-hydroxy-4-(hydroxymethyl)-5-methylenecyclopentyl)-1H-purin-6(9H)-one (FMCG, 11)

Compound 9G (70 mg, 0.116 mmol) was dissolved in a mixture of trifluoroacetic acid and water (5 mL, 3:2), and the mixture was stirred at 60 C for 2 h. The solvent was removed under reduced pressure and the residue was purified by column chromatography on silica gel (methanol/DCM 0.2/10 to 0.6/10) to give 11 (23 mg, 70%) as off white solid; [α] 25D=+140 (c 0.5, MeOH); $^1$H-NMR [500 MHz, CD$_3$OD]: δ 7.67 (s, 1H), 5.73 (d, J=25.0 Hz, 1H), 5.41 (s, 1H), 51.6 (s, 0.5H), 4.83 (s, 1H), 4.39 (d, J=12.5 Hz, 1H), 3.84-2.83 (m, 1H), 3.77-3.73 (m, 1H), 2.78 (s, 1H); 19F NMR (500 MHz, DMSO-d6) δ−190.21 (ddd, J=14.0, 28.0, and 56.0 Hz, 1F); MS (ESI) m/z: 296.2 [M+H]$^+$;

FIRST SET OF REFERENCES (1) http://www.who.int/mediacentre/factsheets/fs204/en/.
(2) Bhattacharya, D.; Thio, C. L. *Clinical Infectious Diseases* 2010, 51, 120.
(3) Kim, K. H.; Kim, N. D.; Seong, B. L. *Molecules* 2010, 15, 5878.
(4) Mukaide, M.; Tanaka, Y.; Shin-I, T.; Yuen, M. F.; Kurbanov, F.; Yokosuka, O.; Sata, M.; Karino, Y.; Yamada, G.; Sakaguchi, K.; Orito, E.; Inoue, M.; Baqai, S.; Lai, C. L.; Mizokami, M. *Antimicrob. Agents Ch* 2010, 54, 882.
(5) Bartholomeusz, A.; Locarnini, S. *Journal of Medical Virology* 2006, 78, S52.
(6) Wang, J. N.; Singh, U. S.; Rawal, R. K.; Sugiyama, M.; Yoo, J.; Jha, A. K.; Scroggin, M.; Huang, Z. H.; Murray, M. G.; Govindarajan, R.; Tanaka, Y.; Korba, B.; Chu, C. K. *Bioorg. Med. Chem Lett.* 2011, 21, 6328.
(7) Rawal, R. K.; Singh, U. S.; Chavre, S. N.; Wang, J. N.; Sugiyama, M.; Hung, W.; Govindarajan, R.; Korba, B.; Tanaka, Y.; Chu, C. K. *Bioorg. Med. Chem. Lett.* 2013, 23, 503.
(8) Walsh, A. W.; Langley, D. R.; Colonno, R. J.; Tenney, D. J. *PLoS. One* 2010,
(9) Jin, Y. H.; Liu, P.; Wang, J. N.; Baker, R.; Huggins, J.; Chu, C. K. *J. Org. Chem.* 2003, 68, 9012.
(10) Jin, Y. H.; Chu, C. K. *Nucleos. Nucleot. Nucl.* 2003, 22, 771.
(11) Gadthula, S.; Rawal, R. K.; Sharon, A.; Wu, D.; Korba, B.; Chu, C. K. *Bioorg. Med. Chem. Lett.* 2011, 21, 3982.

Examples Continued

Figure 2:
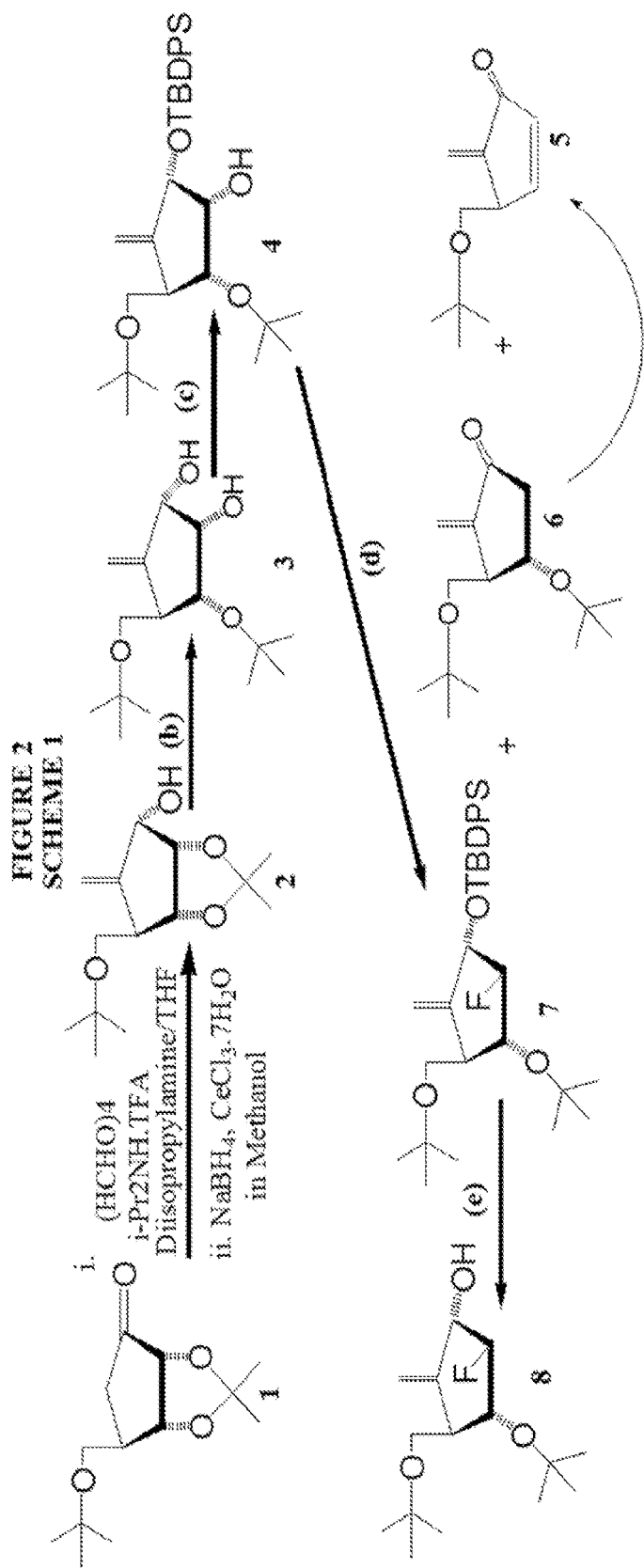
FIG. 2, Scheme 1, shows the synthetic chemical scheme for preparing compound 8 from compound 1. The first step utilizes paraformaldehyde, diisopropylammonium trifluoroacetate salt and diisopropylamine in THF to introduce the olefinic group at the six position (unsubstituted carbon position) of the cycloheptyl ring. All of the remaining steps are similar to those same chemical steps in FIG. 1, Scheme 1A. Reagents and conditions: (b) Al(Me)$_3$ (2.0 M in hexane), THF; (c) TBDPSC1, imidazole, DCM; (d) DAST, DCM; and (e) TBAF, THF.
Figure 3:
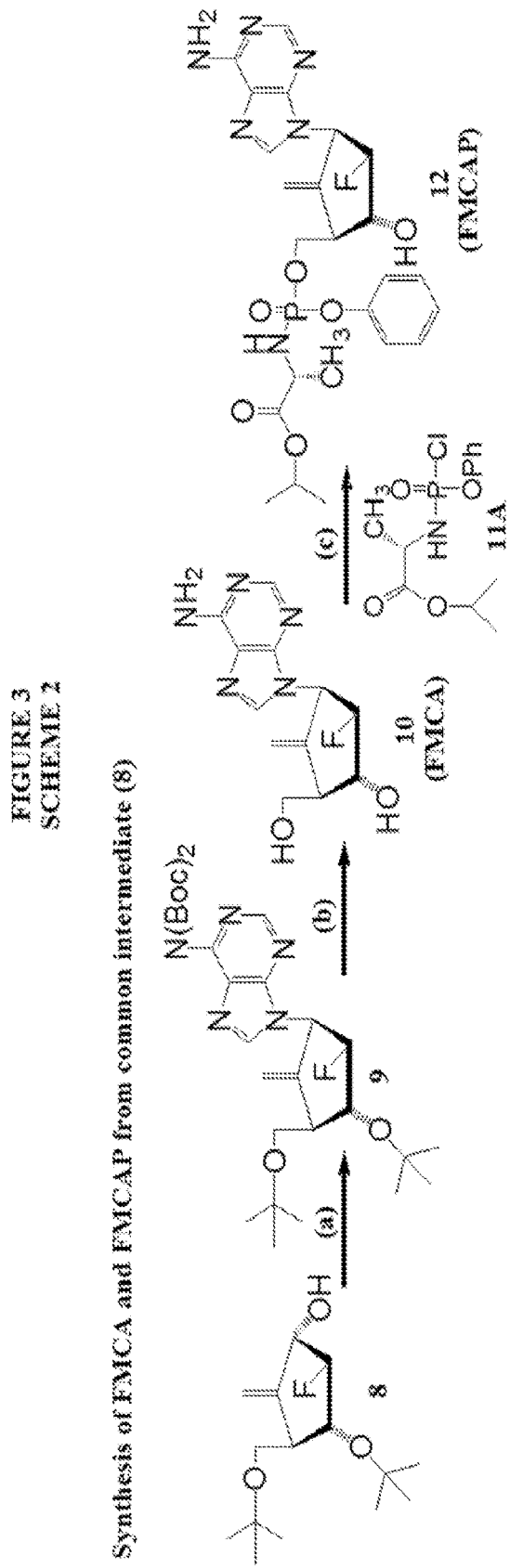
FIG. 3, Scheme 2, shows the synthesis of FMCA (compound 10) and FMCAP (compound 11) from intermediate compound 8 to provide in a first step compound 9 which condenses a diblocked (Boc) adenine onto compound 8, followed by deprotection of the amine and hydroxyl groups to provide FMCA, which may be reacted with intermediate 11A to provide the prodrug FMCAP (compound 12). Reactions and conditions: (a) diBoc-adenine, DIAD, TPP, THF; (b) TFA, DCM; (c) Compound 11A, NMI, THF, FIG. 4, Scheme 3, shows a proposed mechanism for the formation of compound 5 and compound 6 starting from compound 4.

Second Set of Examples (Associated with FIGS. 2 and 3, Schemes 1 and 2)

Second Set of References Applies

The inventors have published an efficient and stereoselective synthesis of FMCA via Vince Lactam.[13] Although, poor yields of the diazotization-elimination step of an amino group including with the inversion of configuration of the hydroxy group in previously explained synthesis by Vince lactam, makes that synthetic route incapable for large scale synthesis of FMCA. In the search of new realistic approaches for the synthesis of FMCA, then inventors' research group revisited all the synthetic possibilities that can be utilized for a substantial synthesis of this nucleoside. In this set of examples, the inventors report a viable and highly practical synthesis of FMCA via intermediate 8 that may be employed in industrial scale synthesis. The currently described route has a better yield and fewer steps in terms of intermediate formation and has escaped expensive column chromatography purification efficiently in some steps. These improvements provide a more competent synthetic route for large scale synthesis of FMCA. As it was elucidated in a previous communication[13], before the condensation with Boc-protected adenine the inversion of hydroxyl group configuration of the key intermediated (Fluoro sugar) was required, but in the present synthesis, this step is eliminated. Furnished intermediate 8 is directly coupled with di-Boc adenine under Mitsunobu coupling conditions producing targeted nucleoside in good yield. By eliminating these issues from the previous synthetic route, the present synthesis is far more practical and feasible for large scale synthesis of FMCA in 7 steps.

Compound 1 is commercially available. The synthesis of compound 2 was carried out by introduction of an exocyclic methylene group in ketone 1 at the 6 position of the compound (5-position of the cyclopentane moiety). In one method, the incorporation of the exocyclic double bond was performed by treatment of ketone 1 with Eschenmoser's salt in the presence of LDA, followed by Hoffman elimination with methyl iodide. This step was very challenging and tedious; and the excess use of methyl Iodide in large scale synthesis was not cost effective. In the updated synthesis, to avoid these harmful and expensive reagents, the insertion of an exocyclic double bond was performed using paraformaldehyde in the presence of diisopropylamine with TFA as salt.[17] Pursuant to this approach, ketone 1 was treated with paraformaldehyde in the presence of catalytic diisopropyl ammonium trifluoroacetate salt in THF to introduce the double bond at 6 position of ketone and furnish enone 2A in 73% yield. In situ selective reduction of the enone was carried out by using sodium borohydride/cerium chloride hydrate complex ($NaBH_4/CeCl_3.7H_2O$) via Luche reduction[18] to give the exclusively α-hydroxyl compound 2 in 90% yield. A regioselective opening of the isopropylidene of compound 2 was accomplished by reported protocol of Ogasawara et al.[19] The treatment of compound 2 with trimethylaluminum (2M solution in hexane) produces diol compound 3 with retention of the α-configuration of hydroxyl groups in 76-77% yield. Selective protection of allylic alcohol of 3 was carried out with tetra-butyl-diphenyl silyl (TBDPS). Diol 3 was treated with TBDPSC1 in presence of the imidazole in DCM at 0° C. to room temperature to give protected compound 4 in up to 92% yield. Due to the higher reactivity of the allylic alcohol and bulkier protecting TBDPS group, 3-hydoxy group protection of compound 3 was unnecessary and exclusively gives the allylic hydroxy protected compound 4.

The next step was the incorporation of fluorine at the 2-position of intermediate 4. Conversion of 2-α-hydroxy to 2-β-fluoro intermediate 7 was accomplished by treating 4 with diethylaminosulfur trifluoride (DAST) at −20° C. to room temperature for 40 minutes, producing compound 7 in 36% yield. Though during the course of this fluorination reaction an interesting observation has been obtained and that is noteworthy to report. The fluorination of compound 4 was carried out by DAST in DCM, to complete consumption of the starting material, reaction was prolong and it has been monitored that simultaneously two polar spots were also appeared on TLC in good yield along with desired compound 7. These results prompted us to isolate and identify the produced polar spots during the course of fluorination. Both the polar spots were purified and their structure elucidation was done by the various analytical techniques. All the analytical data confirm the formation of compound 5 and 6. See FIG. 2, Scheme 1. Interestingly, intermediate 6 is a very worthy carbocyclic sugar in terms of medicinal chemistry interest. In past 2 decades, it is well noted in the literature that preparation of 2-deoxy carbocyclic sugars are very challenging. Compound 6 is 2-deoxy carbocyclic sugar, that may be utilized for the synthesis of various derivative of nucleos(t)ides of medicinal importance. For example, after selective reduction of compound 6 would yield an important 2-deoxy-carbocylic sugar that can be applied for the synthesis of well known anti-hepatitis drug Entecavir.[15,16]

The structure confirmation of compound 6 was validated by $^1H$ NMR, $^1H$-$^1H$ COSY, carbon DEPT and HSQC spectroscopy. The $^1H$ NMR spectrum of compound 6 revealed double doublet of two H-2 protons at δ 2.72 and a quadrate of H-3 proton at δ 4.17 ppm with a complete absence of H-1proton, $^1H$-$^1H$ COSY spectra of 6 showed the correlation of double doublet of H-2 protons with the quadrate of H-3 protons. $^{19}F$-NMR of 6 showed a complete disappearance of fluorine atom confirms the elimination of fluorine and double doublets of H-2 protons proves the formation of 2-deoxy sugar 6. For further confirmation a carbon DEPT experiment was performed which showed three peaks $CH_2$ carbon at 118.4, 61.1, 47.5 and two peaks of the CH carbon at 68.1 and 50.4. The HSQC spectra also revealed that double doublet of two H-2 protons at δ 2.72 showed correlations with $CH_2$ carbon at 47.5 confirms the structure of ketone 6.

Compound 5 was also confirmed by similar analytic techniques. $^1H$ NMR of compound 5 showed two doublets of H-2 and H-3 protons at δ 7.70 and δ 6.44 discloses the formation of olefinic protons. The complete absence of 3-O-tert-butyl protons was appeared by $^1H$-NMR. Probably in an acidic medium elimination of 3-O-tert-butyl group was happening that gives a positive force for formation of conjugated olefinic compound 5. In the $^1H$-$^1H$ COSY spectrum, this olefinic H-2 and H-3 protons showed a clear correlation also confirm adjacent position protons to each other. Furthermore, to confirm the structure of compound 5, Carbon DEPT and HSQC experiment were performed. Wherein, in DEPT experiment two $CH_2$ were exposed at δ 117.7, 64.0 and three CH was obtained at δ 160.9, 135.7 and 45.8 along with single $CH_3$ at 27.5 ppm. In the HSQC spectrum, carbon at 1160.9 showed correlation with a doublet of H-3 proton at δ 7.70 and Carbon at 135.7 showed correlation with the doublet proton of H-2 at δ 6.44 proves elimination of 3-O-tert-butyl group with formation of conjugated alkene of ketone 5. A plausible mechanism of formation of compound 5 and 6 has been shown in Scheme 3. Compound 5 may also be used as a sugar synthon for the synthesis of derived nucleo(t)side.

TBDPS deprotection of compound 7 was done by tetra-butyl ammonium fluoride (TBAF). Compound 7 was treated with a 2M solution of TBAF in THF at room temperature to provides compound 8 in 87% yield. For this synthesis, compound 8 was served as key intermediate. This is condensed with N,N-diBoc protected adenine under Mitsunobu coupling conditions using diisopropyl azodicarboxylate (DIAD) and triphenylphosphine (TPP) in THF produces 9 in 74% yield (Scheme-2). The tert-butyl and Boc protecting groups of compound 9 were removed by using 2 molar trifluoroacetic acid (TFA) in DCM at room temperature, affording target compound 10 (FMCA) in 80% yield. The phosphoramidate prodrug (FMCAP) was synthesized by condensing FMCA with compound 11A. Compound 11A was furnished by reacting phenyl phosphoryl chloride with L-alanine isopropyl ester in DCM at −78° C. to produce reactant 11. To obtain the prodrug form, FMCA is treated with 11 in presence of N-methyl imidazole (NMI) in THF at room temperature to produces target compound 12 in 61% yield.

CONCLUSION

In terms of further warranted in vivo biological screening of FMCA and FMCAP or alternatively, FMCG and FMCGP against drug-resistant mutant HBV a competent and scalable synthesis of FMCA was needed and is described herein via commercially available ketone 1. The selective opening of a protecting group of compound 2 followed by the allylic protection of 3 gives compound 4 in good yields. Fluorination of compound 4 including with deprotection of TBDPS yields key intermediate 8. This intermediate, using Mitsunobu coupling with Boc-protected adenine, followed by the deprotection gives target compound 10 (FMCA) in 7 steps with approximately 6.7% overall yield. Further coupling of Phosphorochloridate 11A with FMCA produces phosphoramidate pro-drug 12 (FMCAP) in good yield. The reduction of steps and use of cheap reagent in the synthesis verifies it is far more convenient for large scale preparation of FMCA than alternative known approaches. During the proficient effort of this synthesis, an important 2'-deoxy sugar 6 has been isolated. Compound 6 may be used in the synthesis of a variety of 2'-deoxy nucleos(t)ides including with synthesis of presently used anti-HBV entecavir drug.

EXPERIMENTAL SECTION

General Analytical Methods

Reagents and anhydrous solvents were purchased and used without further purification. Reactions were monitored by thin-layer chromatography plates (TLC silica gel GF 250 microns) that were visualized using a UV lamp (254 nm) and developed with 15% solution of sulfuric acid in methanol. Melting points were recorded on a digital melting point apparatus and are uncorrected. Nuclear magnetic spectra were recorded on 500 MHz for $^1$H NMR, $^{19}$F NMR and 125 MHz for $^{13}$C NMR with tetramethylsilane as an internal standard. CFCl$_3$ (trichloro-fluoro methane was used as the internal standard (reference) for $^{19}$F-NMR. Chemical shifts (δ) are quoted as s (singlet), bs (broad singlet), d (doublet), t (triplet), q (quartet), m (multiplet), dd (double doublet) and dt (double triplet). Optical rotations were measured on a digital polarimeter. ESI high resolution mass spectra were recorded on a Q-TOF mass spectrometer. Thin layer chromatography was performed on a glass plate coated with silica gel. The following synthetic steps are presented in attached FIG. 2, Scheme 1 and FIG. 3, Scheme 2.

(3aS,4S,6R,6aR)-6-(tert-butoxymethyl)-2,2-dimethyl-5-methylenetetrahydro-3aH-cyclopenta[d][1,3]dioxol-4-ol (2)

To a stirred suspension solution of 1 (50.0 g, 206.6 mmol) and paraformaldehyde (12.4 g, 413.2 mmol) in dry THF was added diisopropyl ammonium trifluoroacetate salt (44.0 g, 206.6 mmol) and diisopropylamine (29.0 mL, 206.6 mmol). The hazy suspension solution was refluxed for 2 h, the mixture became cleared. Then the reaction mixture was cooled to room temperature and added addition portion of paraformaldehyde (12.4 g, 413.2 mmol). The reaction mixture was again refluxed for 12 h. The mixture was concentrated under reduced pressure and residue was diluted with 1 L of ethyl acetate. The Organic layer was washed with water (400 mL×3) and dried over Na$_2$SO$_4$ and concentrated in vacuum. The obtained crude was used as such for next step without further purification. The crude material (52.0 g, 200.7 mmol) was dissolved in anhydrous methanol (500 mL) and added CeCl$_3$.7H$_2$O (98.7 g, 265.0 mmol) at −78° C. and stirred for 20 minutes. After that NaBH$_4$ (9.7 g, 256.9 mmol) was added to this mixture in one portion at −78° C. After 20 minutes stirring at same temperature, reaction mixture was allowed to come to 0° C. and stirred for 30 minutes. A saturated solution of NH$_4$Cl (200 mL) was added and stirred for additional 1 h. The excess organic solvent was removed under reduced pressure and added 10% aqueous acetic acid solution (100 mL). The combined aqueous layer was extracted with ethyl acetate (200 mL×2). The combined organic extract was washed with brine (200 mL×2), dried over Na$_2$SO$_4$ and concentrated under reduced pressure. The residue was purified by silica gel column chromatography (5% EtOAc/hexane) to give compound 2 as a white solid. Yield (27 g, 52% overall yield in 2 steps); $^1$H NMR (500 MHz, CDCl$_3$) δ 5.25 (s, 1H), 5.11 (s, 1H), 4.50-4.53 (m, 3H), 3.46 (dd, J=3.5 & 8.5 Hz, 1H), 3.27 (dd, J=3.5 & 8.5 Hz, 1H), 2.63 (t, J=3.5 Hz, 1H), 2.25 (d, J=11.0 Hz, 1H), 1.40 (s, 3H), 1.34 (s, 3H), 1.12 (s, 9H); $^{13}$C{$^1$H} NMR (125 MHz, CDCl$_3$) δ 153.9, 110.2, 109.3, 81.6, 79.3, 73.8, 72.7, 64.3, 49.9, 27.3, 26.5, 24.7; HRMS (EI) Calcd for (C$_{14}$H$_{24}$O$_4$+Na)$^+$ 279.1572, found 279.1577.

(1S,2S,3R,4R)-3-tert-butoxy-4-(tert-butoxymethyl)-5-methylenecyclopentane-1,2-diol (3)

Compound 2 (40.0 g, 156.2 mmol) was dissolved in 500 ml of DCM and cooled to −78° C. on an ice bath followed by the addition of trimethylaluminum solution (2M solution in hexane, 986.0 mL, 1562.5 mmol). This reaction was warmed to room temperature and stirred for 72 h. The reaction was again cooled to −78° C. and quenched with 200 mL saturated ammonium chloride solution. After that reaction mixture was passed through celite bed and bed was thoroughly washed with dichloromethane (250 mL×2). Filtrate was dried over Na$_2$SO$_4$, concentrated under reduced pressures. The crude was purified by silica gel column chromatography (10% EtOAc/hexane) afforded compound 3 as off-white solid. Yield (32.4 g, 76%). $[α]^{24}_D$=70.24 (c 1.0, CHCl$_3$); $^1$H-NMR (500 MHz, CDCL$_3$) δ 5.34 (s, 1H), 5.12 (s, 1H), 4.26 (d, J=10.0 Hz, 1H), 4.07-4.05 (m, 1H), 3.95-3.92 (m, 1H), 3.46 (dd, J=4.0 & 8.5 Hz, 1H), 3.37 (dd, J=5.0 & 8.0 Hz, 1H), 2.88 (d, J=2.0 Hz, 1H), 2.65 (bs, 1H), 2.50 (d, J=11.0 Hz, 1H), 1.27 (s, 9H), 1.17 (s, 9H); $^{13}$C{H} NMR (125 MHz, CDCl$_3$) δ 152.4, 150.0, 109.9, 75.8, 74.9, 72.4, 62.2, 48.8, 28.5, 27.5; HRMS (EI) Calcd for (C$_{15}$H$_{28}$O$_4$+Na)$^+$ 295.1885, found 295.1882.

(1R,2R,3R,5S)-2-tert-butoxy-3-(tert-butoxymethyl)-5-(tert-butyldiphenylsilyloxy)-4-methylenecyclopentanol (4)

In a solution of compound 3 (20.0 g, 73.5 mmol) in anhydrous methylene chloride (250 mL) at 0° C. was added imidazole (20.0 g, 294.1 mmol) and stirred for 15 minutes. To this solution was added tert-butyldiphenylsilyl chloride (28.7 mL, 110.2 mmol) and the mixture was stirred for 2 h at room temperature. The reaction mixture was diluted with water (300 mL) and separated organic layer was washed with water (200 mL×2) and dried over Na$_2$SO$_4$, concentrated under reduced pressure. Crude was purified by silica gel column chromatography (3% EtOAc/Hexane) to give 4 as oil. Yield: (34.6 g, 92%). $[α]^{24}_D$=16.42 (c 1.0, CHCl$_3$); $^1$H-NMR (500 MHz, CDCl$_3$) δ 7.80-7.78 (m, 2H), 7.74-7.71 (m, 3H), 7.43-7.35 (m, 5H), 5.19 (s, 1H), 5.00 (s, 1H), 4.36 (s, 1H), 3.82-3.79 (m, 1H), 3.56 (s, 1H), 3.36-3.33 (m, 2H), 2.70 (d, J=2.0 Hz, 1H), 2.57 (s, 1H), 1.13 (s, 9H), 1.10 (s, 9H), 1.05 (s, 9H); $^{13}$C{$^1$H} NMR (125 MHz, CDCl$_3$) δ 151.6, 135.9, 135.8, 135.3, 134.8, 134.1, 133.6, 129.6, 122.7, 127.5, 74.1, 72.0, 61.8, 28.4, 27.4, 26.9, 26.6, 19.4, 19.0, 14.1; HRMS (EI) Calcd for (C$_{31}$H$_{46}$O$_4$Si+Na)$^+$ 533.3063, found 533.3059.

((1S,3R,4R)-3-tert-butoxy-4-(tert-butoxymethyl)-2-fluoro-5-methylenecyclopentyloxy)(tert-butyl)diphenylsilane (7)

To a solution compound 4 (20.0 g, 39.2 mmol) in anhydrous dichloromethane (DCM) was added DAST (36.4 mL, 274.4 mmol) slowly at −30° C., and mixture was warmed to room temperature with stirring for 30 min. The reaction mixture was quenched with ice water at −30° C., organic layer was collected, and the aqueous phase was extracted with DCM (200 mL×2). The combined organic layer was dried over Na$_2$SO$_4$, and the solvent was removed under reduced pressure. The crude residue was purified by flash silica gel column chromatography (1% EtOAc/hexane) to give 7 as yellowish oil. Yield (7.2 g, 36%). The two prominent polar compounds 5 and 6 were also formed in this reaction. The produced polar spots of compound 5 and 6 were isolated by column chromatography. During the purification of compound 7 on an elevated polarity of eluent to 10-20%, EtOAc/hexane gave the purified compound 5 in 25% and compound 6 in 30% yield as an oil. $[\alpha]^{24}{}_D$=−30.17 (c 1.0, CHCl$_3$); $^1$H-NMR (500 MHz, CDCl$_3$) δ 7.75-7.73 (m, 4H), 7.46-7.38 (m, 6H), 5.12 (s, 1H), 4.94 (s, 1H), 4.68 (dt, J=50.0 & 75.0 Hz, 1H), 4.64-4.60 (m, 1H), 4.02-3.99 (m, 1H), 3.42 (dd, J=4.0 & 8.0 Hz, 1H), 3.32 (dd, J=4.0 & 8.5 Hz, 1H), 2.50 (bs, 1H), 1.22 (s, 9H), 1.15 (s, 9H), 1.06 (s, 9H); $^{19}$F-NMR (500 MHz, CDCl$_3$) d-188.8 (dt, J=17.5 & 56.5 Hz, 1F); $^{13}$C{$^1$H} NMR (125 MHz, CDCl$_3$) δ 148.1, 136.0, 135.9, 134.1, 133.6, 129.5, 127.4, 109.1, 103.3 (d, J=191.0 Hz), 73.9, 72.2, 61.9, 48.3, 31.6, 28.8, 27.3, 27.0, 22.6, 19.5; HRMS (EI) Calcd for (C$_{31}$H$_{45}$FO$_3$Si+Na)$^+$ 535.3020, found 535.3017.

(R)-4-(tert-butoxymethyl)-5-methylenecyclopent-2-en-1-one (5)

$^1$H-NMR (500 MHz, CDCl$_3$) δ 7.70 (d, J=6.0 Hz, 1H), 6.44 (d, J=5.5 Hz, 1H), 6.44 (s, 1H), 5.59 (s, 1H), 3.56 (bs, 2H), 3.37 (bs, 1H), 1.22 (s, 9H); $^{13}$C{$^1$H} NMR (125 MHz, CDCl$_3$) δ 196.7, 160.9, 135.7, 117.7, 72.9, 64.0, 45.8, 27.5; HRMS (EI) Calcd for (C$_{11}$H$_{17}$O$_2$+H)$^+$ 181.1229, found 181.1224.

(3R)-4-(tert-butoxy)-3-(tert-butoxymethyl)-2-methylenecyclopental-1-one (6)

$^1$H-NMR (500 MHz, CDCl$_3$) δ 6.12 (s, 1H), 5.43 (s, 1H), 4.17 (q, J=6.0 & 12.0 Hz, 1H), 3.55 (d, J=5.0 Hz, 1H), 2.89-2.86 (m, 1H), 2.72 (dd, J=7.0 & 18.5 Hz, 1H), 2.36 (dd, J=6.0 & 18.0 Hz, 1H), 1.24 (s, 9H), 1.20 (s, 9H); $^{13}$C{$^1$H} NMR (125 MHz, CDCl$_3$) δ 205.1, 1.45.4, 118.4, 74.2, 72.8, 68.3, 61.1, 50.4, 47.5, 28.6, 27.5; HRMS (EI) Calcd for (C$_{15}$H$_{27}$O$_3$+H)$^+$255.1960, found 255.1956.

(1S,3R,4R)-3-tert-butoxy-4-(tert-butoxymethyl)-2-fluoro-5-methylenecyclopentanol (8)

To a solution of compound 7 (9.2 g, 17.9 mmol) in THF was added tetrabutylammonium fluoride (TBAF, 1 M solution in THF) (27.0 mL, 26.95 mmol), and the mixture was stirred at room temperature for 3 h. The solvent was removed under reduced pressure and obtained crude was dissolve in ethyl acetate (250 mL). The organic layer was washed with water (200 mL×2) and finally with brine solution (100 mL), dried over Na$_2$SO$_4$, filtered, and concentrated under reduced pressure. The residue was purified by silica gel column chromatography (4% EtOAc/hexane) to afford compound 8 as white foam. Yield (4.3 g, 87%). $[\alpha]^{24}{}_D$=−76.69 (c 1.0, CHCL$_3$); $^1$H-NMR (500 MHz, CDCl$_3$) δ 5.33 (s, 1H), 5.15 (s, 1H), 3.42-3.40 (m, 1H), 2.65 (bs, 1H), 2.28 (d, J=8.0 Hz, 1H) 1.26 (s, 9H), 1.19 (s, 9H); $^{19}$F-NMR (500 MHz, CDCl$_3$) d-190.6 (dt, J=14.0 & 56.5 Hz, 1F); $^{13}$C{$^1$H} NMR (125 MHz, CDCl$_3$) δ 150.0, 149.0, 102.2 (d, J=189.2 Hz), 74.7, 72.59, 62.0, 48.9, 28.6, 27.4; HRMS (EI) Calcd for (C$_{15}$H$_{27}$FO$_3$+Na)$^+$ 297.1842, found 297.1839.

9-((1R,3R,4R)-3-tert-butoxy-4-(tert-butoxymethyl)-2-fluoro-5-methylenecyclopentyl)-N,N-diboc-9H-purin-6-amine (9)

To a stirred solution of triphenylphosphine (4.78 g, 18.24 mmol), in THF (50 mL) at −10° C., DIAD was added (3.68 g, 18.24 mmol) dropwise, reaction mixture was stirred at this temperatute for 30 minutes, and then a solution of N,N-diBoc-protected adenine (3.6 g, 10.9 mmol) in THF (20 mL) was added. This mixture was stirred for 30 min at 0° C. Then reaction mixture was again cooled to −20° C. and compound 8 (2.0 g, 2.29 mmol) in THF (10 mL) was added dropwise. The reaction temperature was raised to room temperature and stirred for 1.5 h. Reaction was quenched with methanol and solvent was removed under reduced pressure, the crude residue was purified by silica gel column chromatography (5% EtOAc/hexane) to give 9 as a white foam. Yield (3.2 g, 74%). $[\alpha]^{24}{}_D$=−51.47 (c 1.0, CHCl$_3$); $^1$H-NMR (500 MHz, CDCl$_3$) δ 8.91 (s, 1H), 8.24 (s, 1H), 5.97 (d, J=30.5 Hz, 1H), 5.32 (s, 1H), 4.90 (dd, J=9.0 & 52.5 Hz, 1H), 4.49-4.77 (m, 1H), 4.33 (d, J=14.0 Hz, 1H), 3.62-3.60 (m, 1H), 3.54-3.50 (m, 1H), 2.85 (bs, 1H), 1.47 (s, 18H), 1.28 (s, 9H), 1.27 (s, 9H); $^{19}$F-NMR (500 MHz, CDCl$_3$) d-191.1 (ddd, J=17.5, 35.0 & 49.0 Hz, 1F); $^{13}$C{$^1$H} NMR (125 MHz, CDCl$_3$) δ 153.9, 152.0, 150.4, 150.2, 150.0, 146.4, 145.3, 128.1, 111.7, 109.9, 83.7, 75.7, 73.2, 62.6, 49.8, 28.2, 27.8, 27.5; HRMS (EI) Calcd for (C$_{30}$H$_{47}$FN$_5$O$_6$+H)$^+$ 592.3510, found 592.3509.

(+)-9

[(1'R, 2'R, 3'R, 4'R)-2'-Fluoro-3'-hydroxy-4'-(hydroxymethyl)-5'-methylenecyclopentan-1'-yl]adenine (FMCA, 10). Compound 9 (3.3 g, 5.58 mmol) was dissolved in 30 mL of DCM. Added trifluoroacetic acid (6 mL) to this solution and mixture was stirred at room temperature for 16 h. TFA with excess solvent was removed under reduced pressure and residue was co-evaporated three times with methanol to remove residual trifluoroacetic acid and neutralized with 28% aqueous ammonia solution, concentrated under reduced pressure. The obtained crude was purified by column chromatography on silica gel (6% Methanol/DCM) to give 10 as white solid. (Yield 1.2 g, 80%). Mp 215-218° C.; $[\alpha]^{24}{}_D$=+152.10° (c 0.5, MeOH); $^1$H-NMR (500 MHz, CD$_3$OD) δ 8.26 (s, 1H), 8.10 (d, 1H), 5.90 (d, J=26.0 Hz, 1H), 5.46 (s, 1H), 4.96 (dt, J=2.5 & 52.5 Hz, 1H), 4.95 (s, 1H), 4.44 (dd, J=13.5 Hz, 1H), 3.88-3.82 (m, 2H), 2.81 (bs, 1H); $^{19}$F NMR (500 MHz, DMSO-d$_6$) δ−192.93 (ddd, J=14.0, 28.0 & 56.0 Hz, 1F), $^{13}$C{$^1$H} NMR [125 MHz, CD$_3$OD]: δ 51.0, 57.5 (d, J=17.4 Hz), 61.7, 72.9 (d, J=23.6 Hz), 95.9 (d, J=184.0 Hz), 111.7, 117.9, 141.1, (d, J=5.3 Hz), 146.0, 149.9, 152.5, 156.0; HRMS (EI) Calcd, for (C$_{12}$H$_{15}$FN$_5$O$_2$+H)$^+$ 280.1210, found 280.1216.

{[(1R,3R,4R)-3-(6-amino-9H-purin-9-yl)-4-fluoro-5-hydroxy-2-methylenecyclopentyl)methoxy](phenoxyphosphoryl amino} propionic Acid Isopropyl Ester (12)

Phenyl dichlorophosphate (1.0 mol equiv) and the L-alanine isopropyl ester hydrochloride salt (1.0 mol) was taken in anhydrous dichloromethane and cool to −78° C. Added triethylamine (2.0 mol) dropwise at −78° C. and stirred for 1 h. After 1 h the reaction mixture was slowly allowed to warm to room temperature and stirring was continued for 2 h. The solvent was removed under reduced pressure and crude residue was re-suspended in anhydrous ether and filtered through a celite bed under nitrogen. The filtrate was concentrated to produce compound 11, which was used as such for next step. N-Methylimidazole, NMI (0.9 mL, 10.7 mmol) was added to a stirring suspension of compound 10 (0.5 g, 1.79 mmol) in dry THF under argon atmosphere at 0° C. The phosphorochloridate 11 (2.2 g. 7.1 mmol) was added dropwise by dissolving in THF. The reaction mixture was warm up to room temperature and continues stirred overnight. Then volatiles were evaporated under reduced pressure and crude was purified by silica gel column chromatography (2% Methanol/DCM) to give the compound 12 as off-white solid. (Yield 0.55 g, 61%). $^1$H-NMR (500 MHz, CDCl$_3$) δ d 8.36 (s, 1H), 7.84 (d, J=24.5 Hz, 1H), 7.28-7.10 (m, 5H), 5.88 (d, J=30.0 Hz, 1H), 5.80 (bs, 2H), 5.18 (d, J=9.0 Hz, 1H), 4.96-4.76 (m, 3H), 4.39-4.34 (m, 2H), 4.17-4.04 (m, 2H), 3.90-3.88 (m, 2H), 3.00 (bs, 1H), 1.31 (d, j=6.5 Hz, 3H), 1.16 (dd, J=6.0, & 14.0 Hz, 6H); $^{19}$F NMR (500 MHz, CDCl$_3$) δ–192.81 (ddd, j=17.5, 31.5 & 53.0 Hz, 1F); $^{31}$P NMR (CDCl$_3$, 202 MHz): δ 2.84, 2.37; $^{13}$C{$^1$H} NMR [125 MHz, CDCl$_3$]: δ 187.7, 173.3, 155.4, 153.1, 150.5, 144.5, 142.4, 140.9, 129.8, 125.2, 120.3, 118.7, 112.3, 95.9, 73.7, 50.5, 49.6, 21.6, 20.8; HRMS (EI) Calcd for (C$_{24}$H$_{31}$FN$_6$O$_6$P+H)$^+$ 549.2027, found 549.2026.

SECOND SET OF REFERENCES (1) who.int/mediacentre/factsheets/fs204/en/.
(2) Bhattacharya, D.; Thio, C. L. *Clin Infect Dis* 2010, 1, 1201.
(3) Fung, J.; Lai, C. L.; Seto, W. K.; Yuen, M. F. *J Antimicrob Chemoth* 2011, 66, 2715.
(4) Tenney, D. J.; Rose, R. E.; Baldick, C. J.; Levine, S. M.; Pokornowski, K. A.; Walsh, A. W.; Fang, J.; Yu, C. F.; Zhang, S.; Mazzucco, C. E.; Eggers, B.; Hsu, M.; Plym, M. J.; Poundstone, P.; Yang, J.; Colonno, R. J. *Antimicrob Agents Ch* 2007, 51, 902.
(5) Terrault, N. A.; Bzowej, N. H.; Chang, K. M.; Hwang, J. P.; Jonas, M. M.; Murad, M. H. *Hepatology* 2016, 63, 261.
(6) Bin Lee Y.; Lee. J. H.; Lee, D. H.; Cho, H.; Ahm H.; Choi, W. M.; Cho, Y. Y.; Lee, M.; Yoo, J. J.; Cho, Y.; Cho, E. J.; Yu, S. J.; Kim, Y. J. Yoon, J. H.; Kim, C. Y.; Lee, H. S. *Hepatology* 2014, 60, 1115a.
(7) Mukaide, M.; Tanaka, Y.; Shin-I, T., Yuen, M. F.; Kurbanov, F.; Yokosuka, O; Sata, M. Karino, Y.; Yamada, G.; Sakaguchi, K.; Orito, E.; Inoue, M.; Baqai, S.; Lai, C. L.; Mizokami, M. *Antimicrob Agents Ch* 2010, 54, 882.
(8) Lazarevic, I. *World J Gastroentero* 2014, 20, 7653.
(9) Wang, J. N.; Singh, U. S.; Rawal, R. K.; Sugiyama, M.; Yoo, J.; Jha, A. K.; Scroggin, M.; Huang, Z. H.; Murray, M. G.; Govindarajan, R.; Tanaka, Y.; Korba, B.; Chu, C. K. *Bioorg Med Chem Lett* 2011, 21, 6328.
(10) McGuigan, C.; Gilles, A.; Madela, K.; Aljarah, M.; Holl, S.; Jones, S.; Vernachio, J.; Hutchins, J.; Ames, B.; Bryant, K. D.; Gorovits, E.; Ganguly, B.; Hunley, D.; Hall, A.; Kolykhalov, A.; Liu, Y. L.; Muhammad, J.; Raja, N.; Walters, R.; Wang, J.; Chamberlain, S.; Henson, G. *J Med Chem* 2010, 53, 4949.
(11) Chang, W.; Bao, D. H.; Chun, B. K.; Naduthambi, D.; Nagarathnam, D.; Rachakonda. S.; Reddy, P. G.; Ross, B. S.; Zhang, H. R.; Bansal, S.; Espiritu, C. L.; Keilman, M.; Lam, A. M.; Niu, C.; Stetter, H. M.; Furman, P. A.; Otto, M. J.; Sofia, M. J. *Acs Med Chem Lett* 2011, 2, 130.
(12) Rawal, R. K.; Singh, U. S.; Chavre, S. N.; Wang, J. N.; Sugiyama, M.; Hung, W.; Govindarajan, R.; Korba, B.; Tanaka, Y.; Chu, C. K. *Bioorg Med Chem Lett* 2013, 23, 503.
(13) Singh, U. S.; Mishra, R. C.; Shankar, R.; Chu, C. K. *J Org Chem* 2014, 79, 3917.
(14) Jin, Y. H.; Liu, P.; Wang, J. N.; Baker, R.; Huggins, J.; Chu, C. K. *J Org Chem* 2003, 68, 9012.
(15) Velasco, J.; Ariza, X.; Badia, L.; Bartra, M.; Berenguer, R.; Farras, J.; Gallardo, J.; Garcia, S.; Gasanz, Y. *J Org Chem* 2013, 78, 5482.
(16) Zhou, B.; Li, Y, C. *Tetrahedron Lett* 2012, 53, 502.
(17) Bugarin, A.; Jones, K. D.; Connell, B. T. *Chem Commun* 2010, 46, 1715.
(18) Genial, A. L.; Luche, J. L. *J Am Chem Soc* 1981, 103, 5454.
(19) Takano, S.; Ohkawa, T.; Ogasawara, K. *Tetrahedron Lett* 1988, 29, 1823.

What is claimed is:

1. A process for preparing the compound 2'-Fluoro-6'-Methylene-Carbocyclic Adenosine (FMCA) compound 10

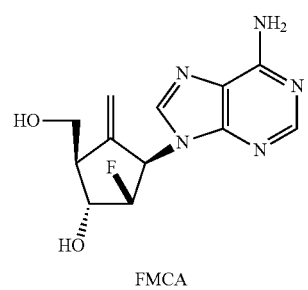

from compound 8

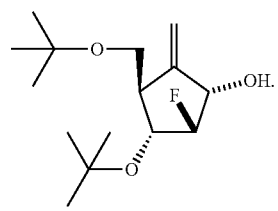

Comprising condensing an amine protected 6-amino purine compound according to the chemical structure:

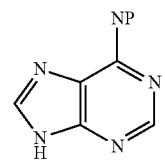

where P represents one or two amine protecting groups onto compound 8 in the presence of triphenylphosphine and diisopropylazidocarboxylate (DIAD) in solvent to produce compound 8P

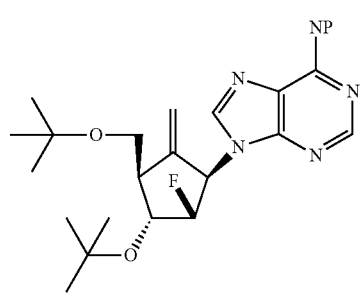

where P represents one or two amine protecting groups; and subjecting compound 8P to deprotection to produce compound 10 (FMCA)

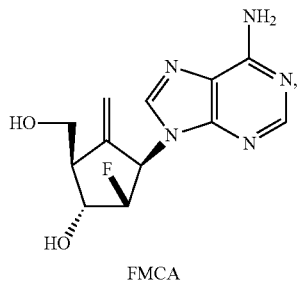

FMCA wherein the synthesis may be conducted in a single pot or in steps, with separation and/or purification to produce either of compounds 8P and compound 10.

2. The process according to claim 1 wherein compound 8P is

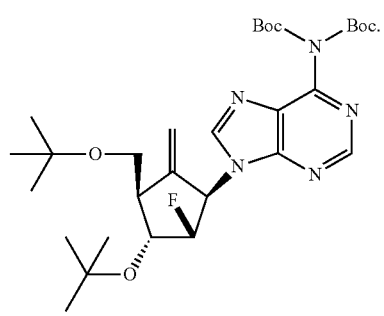

compound 9

3. A process for preparing the compound 2'-Fluoro-6'-Methylene-Carbocyclic Adenosine (FMCA) compound 10

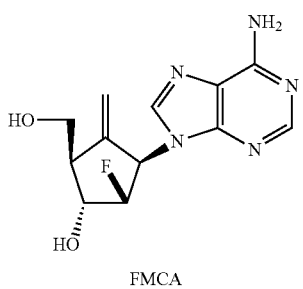

FMCA from compound 8

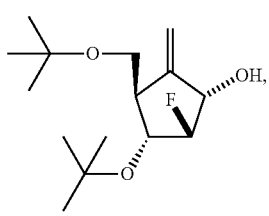

Comprising condensing a di-Boc protected 6-amino purine compound according to the chemical structure:

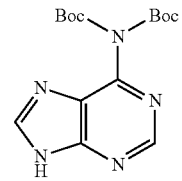 [SMILES: CC(C)(C)OC(=O)N(C(=O)OC(C)(C)C)c1ncnc2[nH]cnc12]

onto compound 8 in the presence of triphenylphosphine and diisopropylazidocarboxylate (DIAD) in solvent to produce compound 9

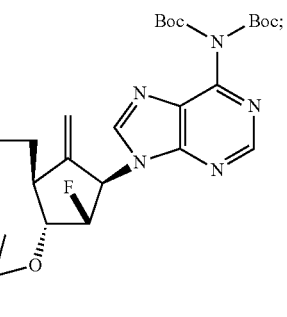

and subjecting compound 9 to deprotection to produce compound 10 (FMCA)

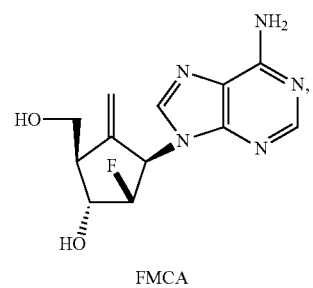

FMCA wherein the synthesis may be conducted in a single pot or in steps, with separation and/or purification to produce compound 9 and/or compound 10.

4. The method of claim 3 wherein at least compound 10 is purified and isolated.

5. The method according to claim 1 wherein compound 8P is separated and purified.

6. The method according to claim 3 wherein compound 9 is separated and purified.

7. The method according to claim 1 wherein compound 10 is separated and purified.

8. The method according to claim 1 wherein said deprotection step occurs in the presence of trifluoroacetic acid and water in solvent at elevated temperature.

9. The method according to claim 1 wherein FMCA (compound 10) is further reacted with a chlorophenylphosphoryl-L-alaninate reactant according to the chemical structure:

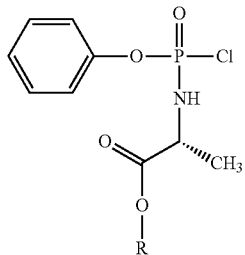

where R is a $C_1$-$C_{20}$ alkyl group and the phenyl group is optionally substituted in the presence of weak base in solvent to produce the 5'-0-phosphoramidate prodrug form of FMCA:

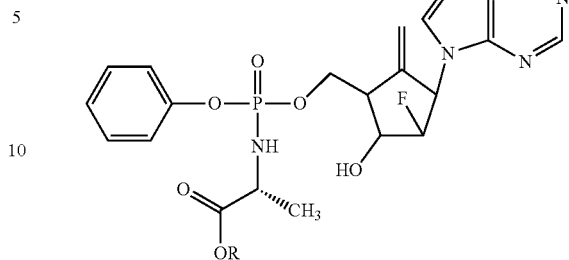

where R is $C_1$-$C_{20}$ alkyl group, or
a pharmaceutically acceptable salt or stereoisomer thereof.

10. The method according to claim 1 wherein P represents two amine protecting groups.

11. The method according to claim 1 wherein P represents two Tert-butyloxylcarbonyl (BOC) protecting groups.

* * * * *